[12] United States Patent
Matsushita et al.

(10) Patent No.: US 11,419,570 B2
(45) Date of Patent: Aug. 23, 2022

(54) RADIATION IMAGE CAPTURING SYSTEM

(71) Applicant: Konica Minolta, Inc., Tokyo (JP)

(72) Inventors: Wataru Matsushita, Hino (JP); Kenroku Ubukata, Hachioji (JP); Hidetake Tezuka, Tachikawa (JP); Tomonori Gido, Kawasaki (JP); Fumikage Uchida, Asaka (JP); Hisashi Yonekawa, Hachioji (JP); Hirotaka Hara, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 77 days.

(21) Appl. No.: 16/928,398

(22) Filed: Jul. 14, 2020

(65) Prior Publication Data
US 2020/0337669 A1   Oct. 29, 2020

Related U.S. Application Data

(60) Division of application No. 16/272,220, filed on Feb. 11, 2019, which is a continuation of application No.
(Continued)

(30) Foreign Application Priority Data

Sep. 17, 2014  (JP) .................. 2014-188391

(51) Int. Cl.
*A61B 6/00* (2006.01)
(52) U.S. Cl.
CPC .............. *A61B 6/56* (2013.01); *A61B 6/4233* (2013.01); *A61B 6/4266* (2013.01);
(Continued)

(58) Field of Classification Search
None
See application file for complete search history.

(56) References Cited

U.S. PATENT DOCUMENTS 6,269,177 B1  7/2001 Dewaele et al.
6,273,606 B1  8/2001 Dewaele
(Continued)

FOREIGN PATENT DOCUMENTS

JP     H11244269 A    9/1999
JP     2000292546 A  10/2000
(Continued)

OTHER PUBLICATIONS

Extended European Search Report corresponding to Application No. 15185530.1-1666; dated Feb. 26, 2016.
(Continued)

*Primary Examiner* — Thomas R Artman
(74) *Attorney, Agent, or Firm* — Cantor Colburn LLP

(57) ABSTRACT

A radiation image capturing system includes a capturing room and a console. The capturing room includes a bucky apparatus, a radiation irradiating apparatus and a detecting unit. A plurality of portable radiation image capturing apparatuses can be loaded on the bucky apparatus. The radiation irradiating apparatus is able to simultaneously irradiate radiation to the plurality of portable radiation image capturing apparatuses. The console is associated with the capturing room and obtains capturing order information. The console allows the portable radiation image capturing apparatuses to advance to a capturing possible state when the console judges that capturing in the capturing order information is long length capturing. The console allows only one of the portable radiation image capturing apparatuses to advance to the capturing possible state when the console judges that the capturing is not the long length capturing.

9 Claims, 19 Drawing Sheets

Related U.S. Application Data

14/856,951, filed on Sep. 17, 2015, now Pat. No. 10,342,508.

(52) U.S. Cl.
CPC .......... *A61B 6/4405* (2013.01); *A61B 6/5241* (2013.01); *A61B 6/545* (2013.01); *A61B 6/548* (2013.01); *A61B 6/566* (2013.01)

(56) References Cited

U.S. PATENT DOCUMENTS

| | | | |
|---|---|---|---|
| 6,793,390 | B2 | 9/2004 | Wang et al. |
| 7,498,583 | B2 | 3/2009 | Shoji et al. |
| 7,555,100 | B2 | 6/2009 | Wang et al. |
| 8,351,568 | B2 | 1/2013 | Minnigh et al. |
| 8,461,543 | B2 | 6/2013 | Nishino |
| 8,586,934 | B2 | 11/2013 | Nakatsugawa et al. |
| 8,625,742 | B2 | 1/2014 | Iwashita et al. |
| 8,748,834 | B2 | 6/2014 | Enomoto |
| 9,239,392 | B2 * | 1/2016 | Gemma ................ G01T 1/2006 |
| 9,649,086 | B2 | 5/2017 | Tajima et al. |
| 9,782,144 | B2 | 10/2017 | Kuwabara |
| 9,820,703 | B2 | 11/2017 | Wojcik et al. |
| 9,968,311 | B2 | 5/2018 | Tagawa |
| 10,251,614 | B2 * | 4/2019 | Wojcik ................ A61B 6/4411 |
| 10,342,508 | B2 * | 7/2019 | Matsushita .......... A61B 6/4233 |
| 10,368,829 | B2 * | 8/2019 | Matsushita .......... A61B 6/4233 |
| 2004/0071269 | A1 | 4/2004 | Wang et al. |
| 2006/0219926 | A1 | 10/2006 | Shoji et al. |
| 2008/0152088 | A1 | 6/2008 | Wang et al. |
| 2011/0057111 | A1 | 3/2011 | Nishino |
| 2011/0069814 | A1 * | 3/2011 | Yonekawa ............. A61B 6/566 378/62 |
| 2011/0233415 | A1 | 9/2011 | Nakatsugawa et al. |
| 2011/0286582 | A1 | 11/2011 | Iwashita et al. |
| 2012/0049080 | A1 | 3/2012 | Enomoto |
| 2013/0032696 | A1 | 2/2013 | Tajima |
| 2013/0301802 | A1 | 11/2013 | Eguchi |
| 2015/0245807 | A1 | 9/2015 | Tajima et al. |
| 2015/0245808 | A1 | 9/2015 | Kuwabara |
| 2015/0247936 | A1 * | 9/2015 | Gemma ................ G01T 1/2018 250/363.01 |
| 2016/0074001 | A1 | 3/2016 | Matsushita et al. |
| 2016/0287195 | A1 | 10/2016 | Tagawa et al. |
| 2016/0296190 | A1 * | 10/2016 | Suzuki ................ A61B 6/4283 |
| 2017/0372454 | A1 | 12/2017 | Takagi et al. |
| 2018/0070899 | A1 * | 3/2018 | Wojcik ................ A61B 6/4411 |
| 2019/0029627 | A1 | 1/2019 | Katsushima et al. |
| 2019/0167223 | A1 * | 6/2019 | Matsushita .......... A61B 6/5241 |
| 2019/0167224 | A1 * | 6/2019 | Matsushita .......... A61B 6/5241 |
| 2020/0337669 | A1 * | 10/2020 | Matsushita .......... A61B 6/4233 |

FOREIGN PATENT DOCUMENTS

| | | |
|---|---|---|
| JP | 2005261666 A | 9/2005 |
| JP | 2011072775 A | 4/2011 |
| JP | 2012011057 A | 1/2012 |
| JP | 2012152477 A | 8/2012 |
| JP | 2013094183 A | 5/2013 |
| JP | 2013176407 A | 9/2013 |
| JP | 2013226243 A | 11/2013 |
| JP | 2016059534 A | 4/2016 |
| WO | 2011145171 A1 | 11/2011 |

OTHER PUBLICATIONS

USPTO Non-Final Office Action corresponding to U.S. Appl. No. 14/856,951; dated Apr. 9, 2018.
USPTO Final Office Action corresponding to U.S. Appl. No. 14/856,951; dated Nov. 14, 2018.
USPTO Notice of Allowance for U.S. Appl. No. 14/856,951 dated Mar. 1, 2019.
USPTO Notice of Allowance for U.S. Appl. No. 16/272,195 dated Mar. 29, 2019.
JPO Notification of Reasons for Refusal corresponding to Application No. 2018-114202; dated Apr. 9, 2019.
JPO Notification of Reasons for Refusal corresponding to Application No. 2018-114203; dated Apr. 9, 2019.
JPO Notice of Reasons for Refusal for corresponding JP Application No. 2020-136086; dated Jul. 6, 2021.

* cited by examiner

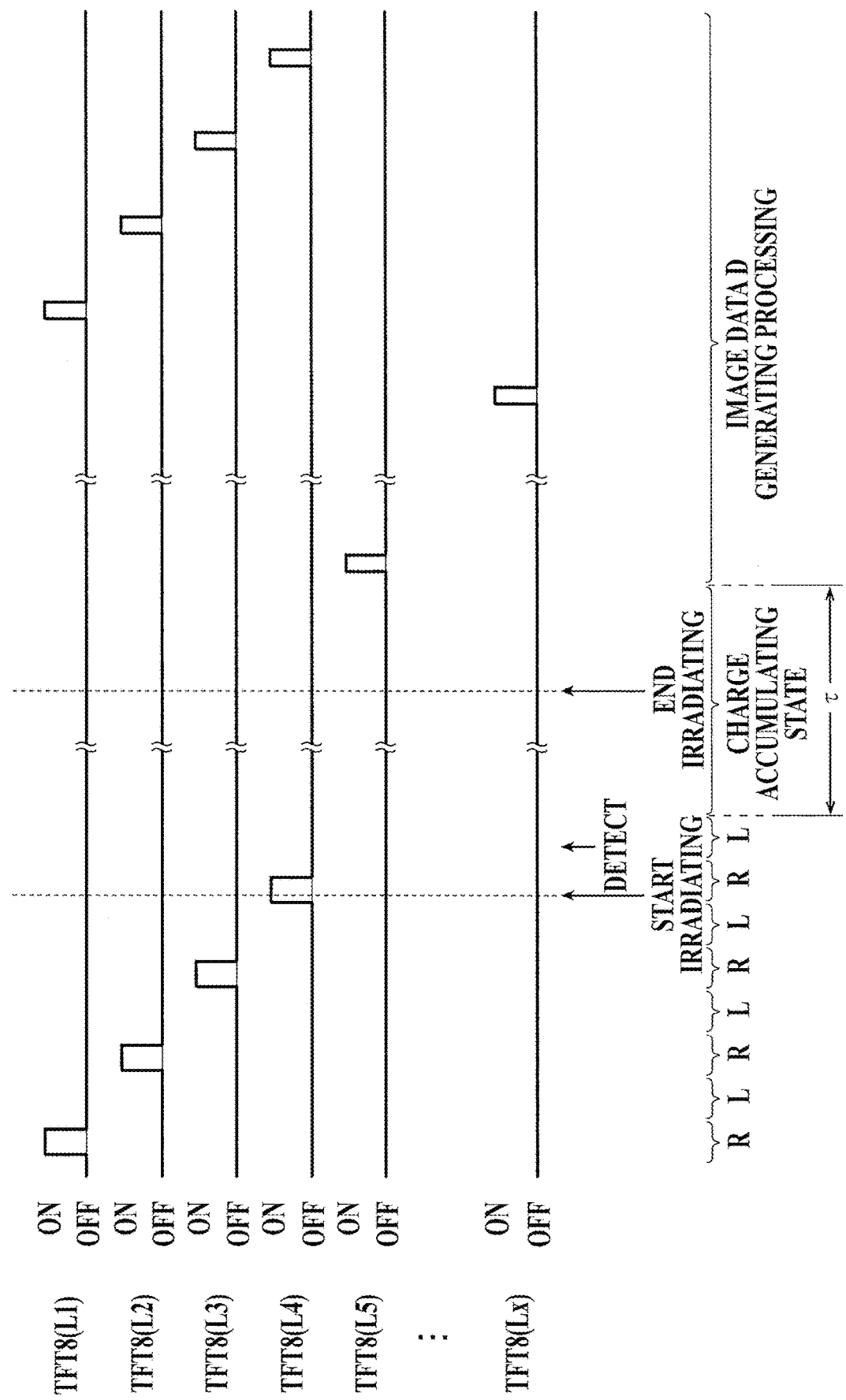

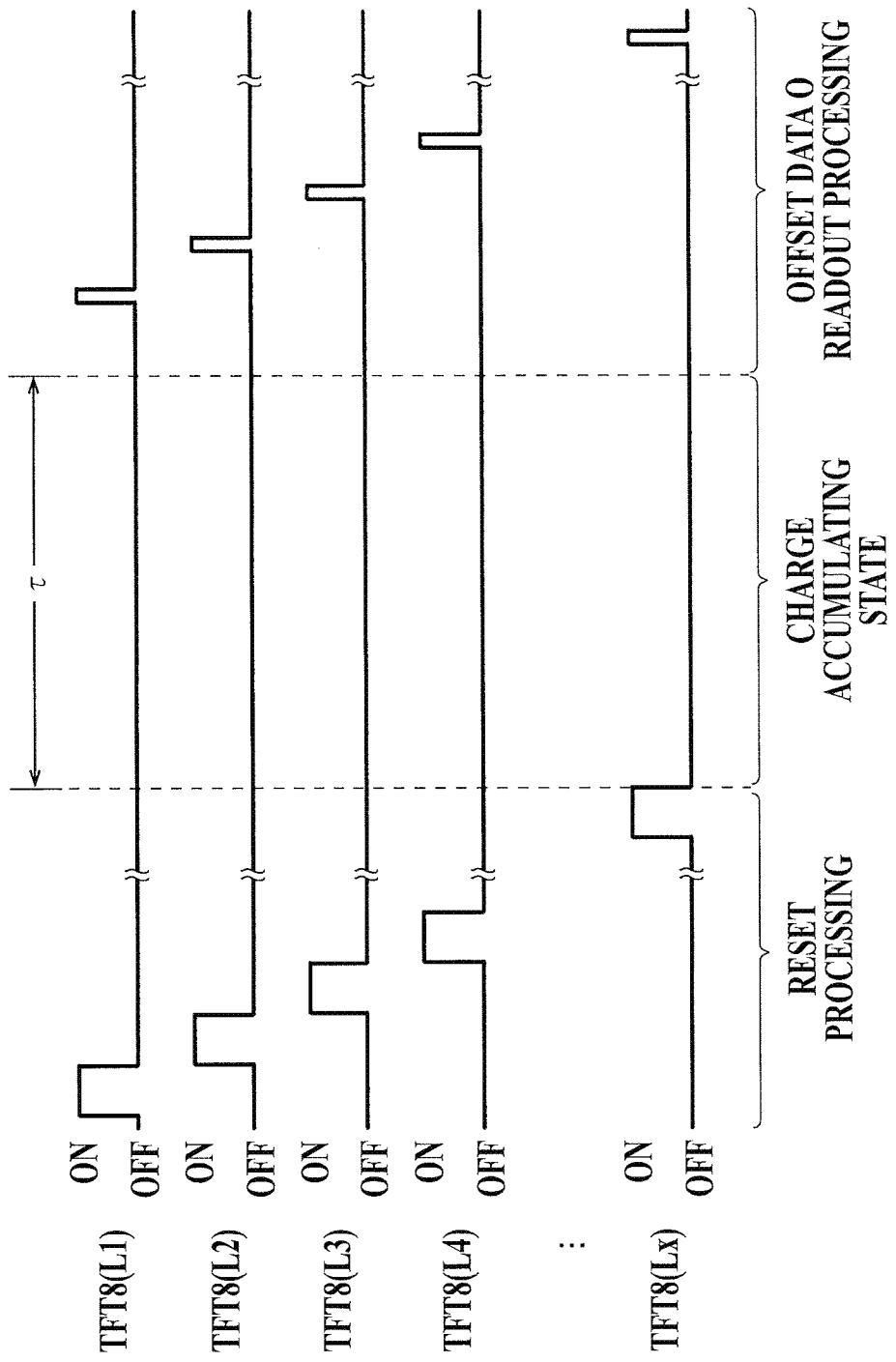

FIG.11

| CAPTURING ORDER ID | PATIENT ID | PATIENT NAME | SEX | AGE | DEPARTMENT | CAPTURING SITE | CAPTURING DIRECTION | POSTURE |
|---|---|---|---|---|---|---|---|---|
| 001 | 100085 | A | MALE | 25 | SURGERY | ENTIRE LOWER EXTREMITY | R FRONT | STANDING POSITION |
| 002 | 100320 | B | FEMALE | 15 | ORTHOPEDICS | LEG | L FRONT | LYING POSITION |
| 003 | 100325 | C | MALE | 60 | ORTHOPEDICS | HAND | L | LYING POSITION |
| 004 | 100085 | A | MALE | 25 | SURGERY | CHEST | FRONT | STANDING POSITION |
| 005 | 100085 | A | MALE | 25 | SURGERY | CERVICAL VERTEBRAE | SIDE R→L | STANDING POSITION |
| 006 | 100085 | A | MALE | 25 | SURGERY | ABDOMEN | FRONT | LYING POSITION |

FIG.12

PLEASE INPUT CAPTURING ORDER INFORMATION OF SCHEDULED CAPTURING    H1

| CAPTURING ORDER ID (P1) | PATIENT ID (P2) | PATIENT NAME (P3) | SEX (P4) | AGE (P5) | DEPARTMENT (P6) | CAPTURING SITE (P7) | CAPTURING DIRECTION (P8) | POSTURE (P9) |
|---|---|---|---|---|---|---|---|---|
| 001 | 100085 | A | MALE | 25 | SURGERY | ENTIRE LOWER EXTREMITY | R FRONT | STANDING POSITION |
| 002 | 100320 | B | FEMALE | 15 | ORTHOPEDICS | LEG | L FRONT | LYING POSITION |
| 003 | 100325 | C | MALE | 60 | ORTHOPEDICS | HAND | L | LYING POSITION |
| 004 | 100085 | A | MALE | 25 | SURGERY | CHEST | FRONT | STANDING POSITION |
| 005 | 100085 | A | MALE | 25 | SURGERY | CERVICAL VERTEBRAE | SIDE R→L | STANDING POSITION |
| 006 | 100085 | A | MALE | 25 | SURGERY | ABDOMEN | FRONT | LYING POSITION |

ENTER (h13)    RETURN (h14)

*(Rotated figure showing a display screen Ca with regions Ia, Ib, H2, I1, I2, I3, I4)*

Screen contents (reading the rotated image):

- CAPTURING ROOM1  TECHNICIAN: ○○ ○○  BIRTHDATE: ○○○○/○○/○○
- PATIENT ID: 100085  AGE: 25 YEARS AND ○ MONTHS
- SEX: MALE
- A  ○○○○/○○/○○
- IMAGE HISTORY
- IRRADIATING CONDITION
- IMAGE QUALITY ADJUSTMENT
- READING CONDITION
- 100 / 300 / 200 / 1.5 (with + / − adjusters)

Panels (each showing 100kV / 200mA / 300ms):

- LONG LENGTH — ENTIRE LOWER EXTREMITY R FRONT — NORMAL/HALF SIZE/VERTICAL/CENTER — OK / NG
- STANDING POSITION — CHEST FRONT — NORMAL/HALF SIZE/VERTICAL/CENTER — OK / NG
- STANDING POSITION — CERVICAL VERTEBRAE SIDE R→L — NORMAL/HALF SIZE/VERTICAL/CENTER — OK / NG
- LYING POSITION — ABDOMEN FRONT — NORMAL/HALF SIZE/VERTICAL/CENTER — OK / NG

Body region selector (Ib): CHEST, THORACIC VERTEBRAE, STERNUM, ELSE

RADIATION IMAGE CAPTURING SYSTEM

CROSS REFERENCE TO RELATED APPLICATIONS

The present application is a divisional application of U.S. patent application Ser. No. 16/272,220 filed Feb. 11, 2019, the entire contents of which are incorporated herein by reference. U.S. application Ser. No. 16/272,220 is a continuation under 35 U.S.C. § 120 of U.S. patent application Ser. No. 14/856,951, filed Sep. 17, 2015, which is incorporated herein by reference and which also claims priority to Japanese Application No. 2014-188391, filed Sep. 17, 2014, priority to which is also claimed herein.

BACKGROUND

Field of the Invention

The present invention relates to a radiation image capturing system. Specifically, the present invention relates to a radiation image capturing system which can perform long length capturing.

Description of Related Art

As a method of capturing a relatively large range such as the upper half or the lower half of the patient, there is known long length capturing in which a radiation image capturing apparatus (Flat Panel Detector) is irradiated with radiation from a radiation irradiating apparatus while changing the position along a body axis of the captured subject and a plurality of radiation images are captured. Usually, the plural radiation images obtained by the long length capturing are connected by image processing to create one radiation image. Various configurations are known as a configuration of a radiation image capturing system to perform such long length capturing. As one example, the radiation image capturing system as described in FIG. 22 is known.

In other words, the radiation image capturing system positions a collimator 102 including an opening (not shown) between a radiation irradiating apparatus 100 and a radiation image capturing apparatus 101. The position of the opening of the collimator 102 is changed by moving the collimator 102 in the body axis direction of a subject H according to the position of the radiation image capturing apparatus 101 being moved along the body axis A of the subject H without changing the irradiating direction and the irradiating region of the radiation from the radiation irradiating apparatus S. An irradiating field of the radiation irradiated from the radiation irradiating apparatus S is limited by the opening of the collimator 102 to only the necessary range including the radiation image capturing apparatus 101. In this state, the radiation is irradiated from the radiation irradiating apparatus S each time the radiation image capturing apparatus 101 changes the position, in other words, radiation is irradiated a plurality of times to capture a plurality of radiation images. A console (not shown) connects the plurality of radiation images to generate one radiation image of long length capturing (for example, see Japanese Patent Application Laid-Open Publication No. 2013-226243).

According to FIG. 22, the radiation image capturing apparatus 101 is moved to two positions vertically to perform capturing. The number of positions the radiation image capturing apparatus 101 is moved to is suitably determined according to the size of the radiation image capturing apparatus 101 used, the capturing site, or the like. Although not shown, the capturing is not limited to a state in which the subject H is standing, in other words a standing position as shown in FIG. 22. For example, similar long length capturing can be performed when capturing is performed in a state in which the subject H is lying down, in other words a lying position.

However, although not limited to the radiation image capturing system using the collimator 102 as shown in FIG. 22, at least in the conventional radiation image capturing system which performs long length capturing by capturing a plurality of radiation images while moving the radiation image capturing apparatus 101 in the body axis A direction of the subject H, the problem of the subject H moving while the radiation image capturing apparatus 101 moves occurs to some extent (in other words, the problem of body movement). When body movement occurs in even one of the plurality of radiation images, even if the one radiation image is captured again and the image combining processing is performed, it is difficult to obtain a suitable long length image. Therefore, all of the plurality of radiation images need to be captured again and the radiation amount on the patient increases.

In order to solve such problem, it is effective to configure the later described radiation image capturing system of the present invention (see later described FIG. 1), in which a plurality of radiation image capturing apparatuses are positioned aligned in the body axis direction (see A in FIG. 1) of the subject and irradiation is irradiated only once (in other words, one shot) from the radiation irradiating apparatus to the radiation image capturing apparatus to capture a plurality of radiation images.

However, from the point of cost effectiveness, it is not easy to newly introduce in facilities such as a hospital a capturing stage to be dedicated to long length capturing provided with a plurality of radiation image capturing apparatuses in the body axis direction of the subject in advance. That is, such capturing stage is costly and the frequency of capturing long length capturing is not high compared to frequency of normal capturing (hereinafter, simple capturing) in which radiation is irradiated once from the radiation irradiating apparatus to one radiation image capturing apparatus.

Therefore, it is preferable to configure a radiation image capturing system in which long length capturing can be performed by using a bucky apparatus for long length capturing already provided in the facilities in which a plurality of CR (Computer Radiography) cassettes are loaded, or cheaply manufacturing a bucky apparatus for long length capturing and loading the necessary number in a portable (also called a cassette type) radiation image capturing apparatus. According to such configuration, the portable radiation image capturing apparatus which can be used in simple capturing which is the main operation in the radiology department can also be used for long length capturing. Therefore, it is possible to enhance cost effectiveness and capturing effectiveness of the entire radiation image capturing system of the radiology department.

However, according to such configuration, various defects may occur in the radiation image capturing system since both simple capturing and long length capturing can be performed using the same portable radiation image capturing apparatus.

SUMMARY

The present invention has been made in consideration of the above problems, and one of the main objects is to provide a radiation image capturing system in which both simple capturing and long length capturing can be accurately performed using a portable radiation image capturing apparatus.

According to one aspect of the present invention, there is provided a radiation image capturing system including:

a capturing room including:
a bucky apparatus on which a plurality of portable radiation image capturing apparatuses can be loaded;
a radiation irradiating apparatus which is able to simultaneously irradiate radiation to the plurality of portable radiation image capturing apparatuses loaded on the bucky apparatus; and
a detecting unit which detects entry of the portable radiation image capturing apparatus; and
a console which is associated with the capturing room, which is able to control the portable radiation image capturing apparatus detected by the detecting unit, and which obtains capturing order information and generates a radiation image based on image data transferred from the portable radiation image capturing apparatus to be associated with the capturing order information; wherein,
the console allows the plurality of portable radiation image capturing apparatuses in the associated capturing room to advance to a capturing possible state when the console judges based on the capturing order information that capturing in the capturing order information is long length capturing which is performed with the plurality of portable radiation image capturing apparatuses loaded on the bucky apparatus; and
the console allows only one of the portable radiation image capturing apparatuses in the associated capturing room to advance to the capturing possible state when the console judges based on the capturing order information that the capturing in the capturing order information is not the long length capturing.

According to another aspect of the present invention, there is provided a radiation image capturing system including:

a capturing room including:
a bucky apparatus on which a plurality of portable radiation image capturing apparatuses can be loaded;
a radiation irradiating apparatus which is able to simultaneously irradiate radiation to the plurality of portable radiation image capturing apparatuses loaded on the bucky apparatus; and
a detecting unit which detects entry of the portable radiation image capturing apparatus; and
a console which is associated with the capturing room, which is able to control the portable radiation image capturing apparatus detected by the detecting unit, and which obtains capturing order information and generates a radiation image based on image data transferred from the portable radiation image capturing apparatus to be associated with the capturing order information; wherein,
the bucky apparatus includes a reading unit which reads identification information of the portable radiation image capturing apparatus loaded in a loading position in which the portable radiation image capturing apparatus is loaded, and the bucky apparatus notifies the identification information to the console when the reading unit reads the identification information of the portable radiation image capturing apparatus loaded in the loading position;
the console judges whether long length capturing which is performed with the plurality of portable radiation image capturing apparatuses loaded on the bucky apparatus can be performed based on the identification information of the portable radiation image capturing apparatus loaded in the loading position, the identification information notified from the bucky apparatus;
the console allows the plurality of portable radiation image capturing apparatuses loaded on the bucky apparatus to advance to a capturing possible state when the console judges that the long length capturing can be performed; and
the console notifies that the long length capturing cannot be performed when the console judges that the long length capturing cannot be performed.

According to another aspect of the present invention, there is provided a radiation image capturing system including:

a plurality of capturing rooms including:
a radiation irradiating apparatus which is able to irradiate radiation to a portable radiation image capturing apparatus; and
a detecting unit which detects entry of the portable radiation image capturing apparatus;
a console which is associated with the capturing room, which is able to control the portable radiation image capturing apparatus detected by the detecting unit, and which obtains capturing order information and generates a radiation image based on image data transferred from the portable radiation image capturing apparatus to be associated with the capturing order information; and
a management apparatus which manages the portable radiation image capturing apparatus in the capturing room based on information of the portable radiation image capturing apparatus detected by the detecting unit provided in each capturing room,
wherein,
any or all of the capturing rooms are provided with a bucky apparatus in which the plurality of portable radiation image capturing apparatuses can be loaded;
the management apparatus judges in which capturing room the long length capturing can be performed based on information of the portable radiation image capturing apparatus and the bucky apparatus in the capturing room and notifies to the console the capturing room which can perform long length capturing in reply to a request from the console which judges based on the capturing order information that the capturing of the capturing order information is the long length capturing which is performed with the plurality of portable radiation image capturing apparatuses loaded on the bucky apparatus; and
the console notifies the information of the capturing room notified from the management apparatus.

According to the radiation image capturing system of the present invention, it is possible to accurately perform both simple capturing and long length capturing using the portable radiation image capturing apparatus.

BRIEF DESCRIPTION OF THE DRAWINGS

The present invention will become more fully understood from the detailed description given hereinbelow and the appended drawings, and thus are not intended to define the limits of the present invention, and wherein;

FIG. 9 is a timing chart describing timing of applying on voltage to each scanning line in a non-linking method in which start of irradiation of radiation is detected based on leak data;

FIG. 10 is a timing chart showing the processing sequence shown in FIG. 8 is repeated and readout processing of offset data is performed;

FIG. 11 is a diagram showing an example of capturing order information;

FIG. 12 is a diagram showing an example of a selection screen which displays capturing order information;

FIG. 13 is a diagram showing an example of a screen which displays each icon corresponding to each piece of capturing order information;

DETAILED DESCRIPTION OF PREFERRED EMBODIMENTS

Figure 1:
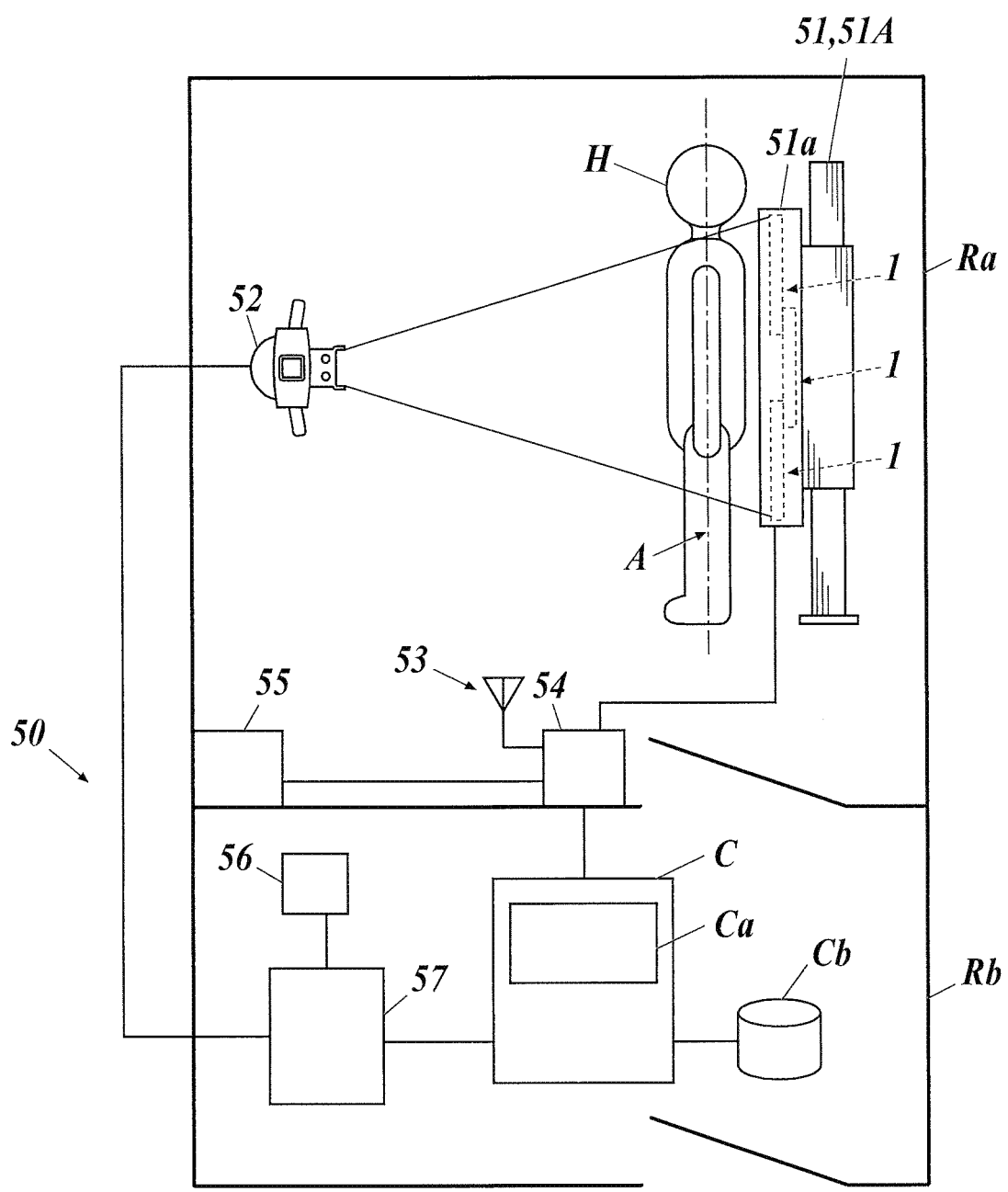
FIG. 1 is a diagram showing a configuration of a radiation image capturing system according to the present embodiment.

An embodiment of a radiation image capturing system of the present invention is described with reference to the drawings. FIG. 1 is a diagram showing a configuration of the radiation image capturing system of the present embodiment.

Figure 2:
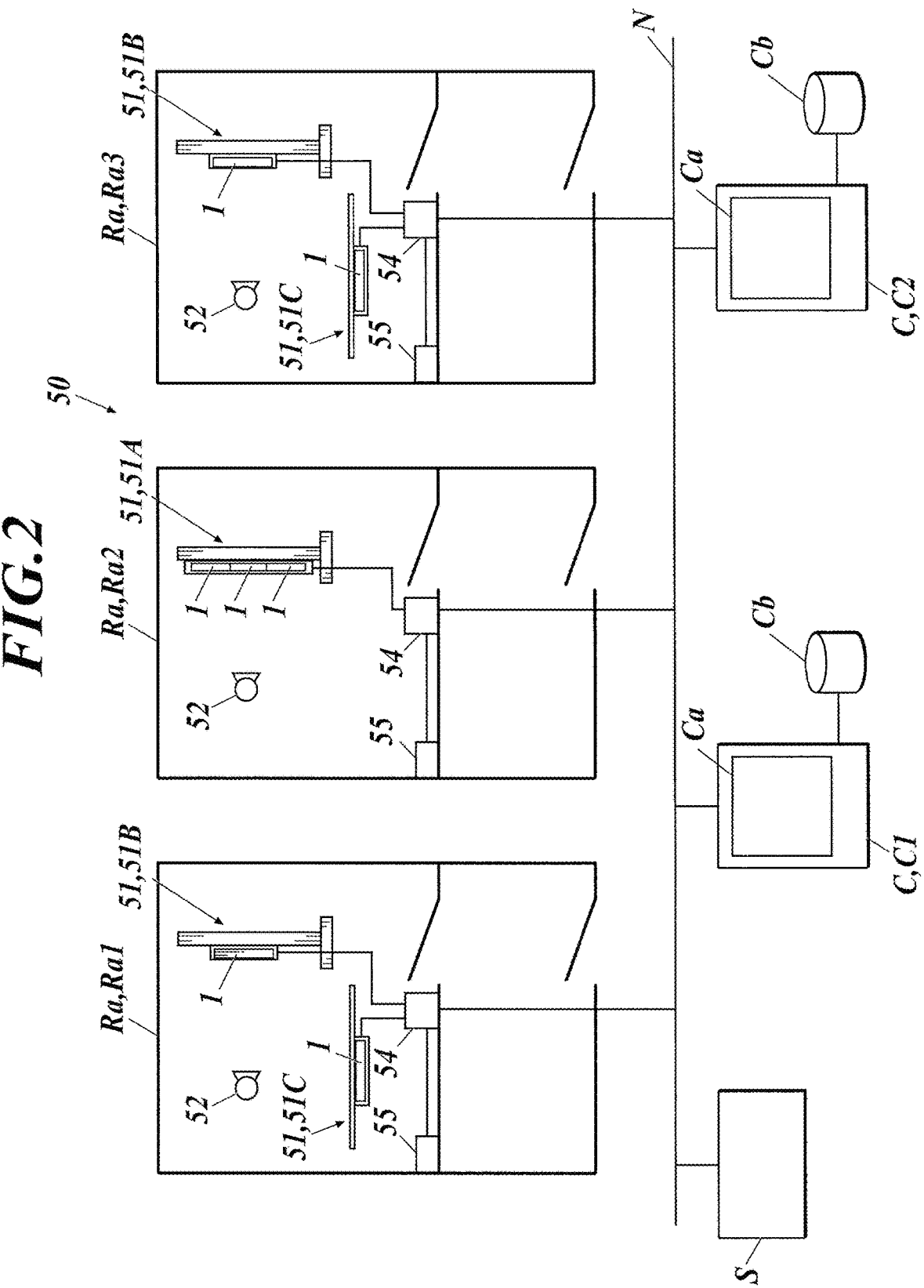
FIG. 2 is a diagram showing an example of a configuration of the radiation image capturing system in which a plurality of capturing rooms are associated with one or a plurality of consoles.

According to the description below, the basic configuration of the radiation image capturing system 50 of the present embodiment includes a capturing room Ra associated with a console C one to one as shown in FIG. 1. The description can be applied to the configuration including a plurality of capturing rooms Ra (Ra1 to Ra3) associated with one or a plurality of consoles C (C1, C2) through a network N, etc. as shown in FIG. 2.

FIG. 1 describes only a bucky apparatus 51A for long length capturing being provided in the capturing room Ra. Alternatively, a bucky apparatus 51B for standing position capturing used in simple capturing and a bucky apparatus 51C (see FIG. 2) for lying position capturing (see FIG. 2) can be provided in the capturing room Ra. In other words, when the capturing room Ra is one room, a bucky apparatus 51A for long length capturing is to be provided in the capturing room Ra, and other modality provided in the capturing room Ra can be suitably determined. When there are a plurality of capturing rooms Ra as shown in FIG. 2, the bucky apparatus 51A for long length capturing is to be provided in at least any one of the capturing rooms Ra. The other modality provided in the above capturing room Ra and other capturing rooms Ra is suitably determined. The bucky apparatus 51A for long length capturing can be provided in all capturing rooms Ra.

As described above, the bucky apparatus 51A for long length capturing can be a bucky apparatus for one long length shot in which a plurality of CR cassettes or film cassettes can be loaded or a bucky apparatus including a conducting or communicating function. The method of use is described in detail below. FIG. 1 and FIG. 2 describe providing a bucky apparatus 51A for long length capturing in a standing position in the capturing room Ra as the bucky apparatus 51A for long length capturing. Although illustration is omitted, the bucky apparatus for long length capturing in a lying position can be provided in the capturing room Ra. The present invention can be applied when the radiation image capturing system 50 is provided with only the bucky apparatus for long length capturing in a lying position as the bucky apparatus 51A for long length capturing.

[Basic Configuration of Radiation Image Capturing System]

As shown in FIG. 1, according to the present embodiment, the bucky apparatus 51A in which a plurality of radiation image capturing apparatuses 1 can be loaded to perform long length capturing is provided in the capturing room Ra (when a plurality of capturing rooms Ra are provided, at least one capturing room Ra). The plurality of radiation image capturing apparatuses 1 can be loaded in the cassette holder 51a of the bucky apparatus 51A for long length capturing so as to be aligned in a body axis A direction of a subject H.

FIG. 1 shows 3 radiation image capturing apparatuses 1 loaded on the cassette holder 51a of the bucky apparatus 51A for long length capturing. However, the number of radiation image capturing apparatuses 1 loaded on the bucky apparatus 51A for long length capturing is not limited to 3. The configuration of the bucky apparatus 51A for long length capturing and the radiation image capturing apparatus 1 is described later.

A radiation irradiating apparatus 52 is provided in the capturing room Ra. As shown in FIG. 1, the radiation irradiating apparatus 52 used in long length capturing is a wide angle irradiating type which can simultaneously irradiate radiation on the plurality of radiation image capturing apparatuses 1 loaded on the bucky apparatus 52A through the subject H (in other words, with one irradiation of radiation (one shot)). The radiation irradiating apparatus 52 for long length capturing can also be used as the radiation irradiating apparatus 52 for standing position capturing or lying position capturing when performing simple capturing. In this case, when simple capturing is performed, the irradiating field of radiation irradiated from the radiation irradiating apparatus 52 for long length capturing can be limited with the collimator and the radiation can be irradiated.

A repeater 54 is provided in the capturing room Ra to relay communication between the apparatuses inside and outside the capturing room Ra. According to the present embodiment, an access point 53 is provided in the repeater 54 so that image data D, signals, etc., can be transmitted and received by the radiation image capturing apparatus 1 wirelessly. The repeater 54 is connected to a radiation irradiating apparatus 55 and console C. A transducer (not shown) which converts the signal transmitted from the radiation image capturing apparatus 1, console C, etc. to the radiation irradiating apparatus 52 for LAN (Local Area Network) communication to a signal for the radiation irradiating apparatus 52 and vice versa is included in the repeater 54.

Figure 3:
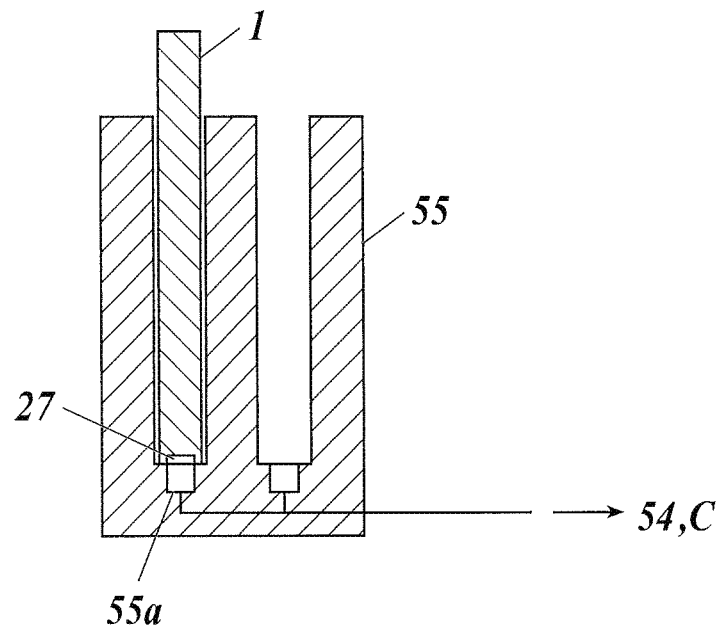
FIG. 3 is a cross-sectional view showing a state in which the radiation image capturing apparatus is inserted in a cradle and connectors are connected to each other.

According to the present embodiment, a cradle 55 is connected to the repeater 54. As shown in FIG. 3, when the radiation image capturing apparatus 1 brought into the capturing room Ra is inserted in the cradle 55 and a later described connector 27 (see later described FIG. 6) of the radiation image capturing apparatus 1 and a connector 55a of the cradle 55 are connected, a cassette ID, etc. which is identification information of the radiation image capturing apparatus 1 is notified to the repeater 54. When the cassette ID of the radiation image capturing apparatus 1 is transmitted from the cradle 55, the repeater 54 notifies the cassette ID to the console C or a later described management apparatus S (see FIG. 2).

The cradle 55 is originally used for storing and charging the radiation image capturing apparatus 1, and according to the present embodiment, the cradle 55 can include a function for charging. Moreover, an SSID of the access point 53 provided in the capturing room R can be notified from the cradle 55, the console C, etc. to the radiation image capturing apparatus 1 when the radiation image capturing apparatus 1 is inserted in the cradle 55. FIG. 3 shows the cradle 55 provided with 2 inserting openings to insert the radiation image capturing apparatus 1. However, the inserting opening provided can be 1 or can be 3 or more. The cradle 55 can be provided in either the capturing room Ra or a front room Rb. When the cradle 55 is provided in the capturing room Ra, the cradle 55 is provided in a position where the radiation irradiated from the radiation irradiating apparatus 52 does not reach the cradle 55, for example, a corner of the capturing room Ra.

Figure 4:
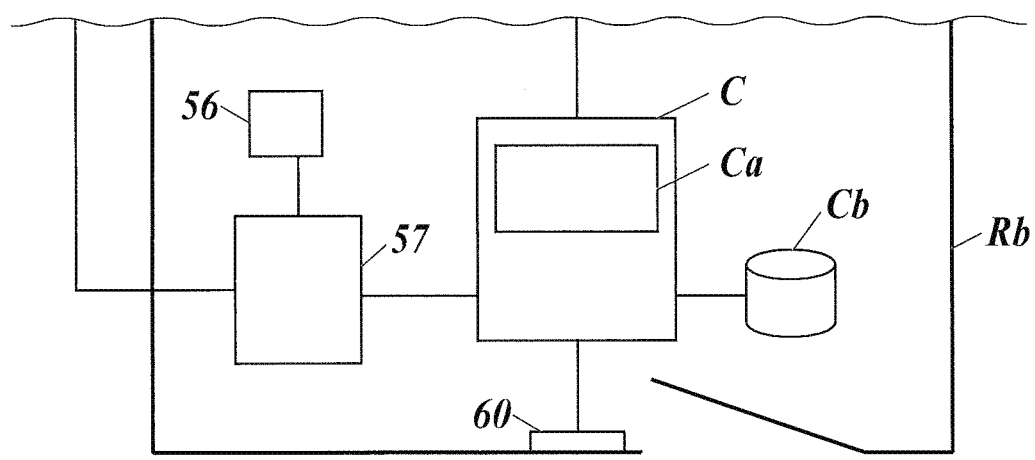
FIG. 4 is a diagram showing an example of a configuration in which a tag reader is provided as a detecting unit.

Instead of using the cradle 55 of the present embodiment as the detecting unit which detects entrance of the radiation image capturing apparatus 1 in the capturing room Ra or the front room Rb, as shown in FIG. 4, for example, a tag reader 60 can be provided near the door of the front room Rb and the capturing room Ra.

In this case, a tag (not shown) such as an RFID tag (Radio Frequency Identification) is included in the radiation image capturing apparatus 1 in advance, and specific information such as the cassette ID of the radiation image capturing apparatus 1 is stored in the tag. When the radiation image capturing apparatus 1 passes near the tag reader 60 and is brought in to or out of the front room Rb and the capturing room Ra, the tag reader 60 can read the information such as the cassette ID from the tag of the radiation image capturing apparatus 1, and notify the cassette ID to the console C or the management apparatus S (see FIG. 2) through the repeater 54.

As shown in FIG. 1, an operation table 57 of the radiation irradiating apparatus is provided in the front room (operation room) Rb and an emitting switch 56 is provided on the operation table 57 to be operated by the user such as the radiology technician, etc. to instruct start of irradiation of radiation to the radiation irradiating apparatus 52. Tube current, irradiating time, etc. for the radiation irradiating apparatus 52 can be set on the operation table 57. According to the present embodiment, the setting of the tube current, etc. can also be performed on the console C.

Figure 5A:
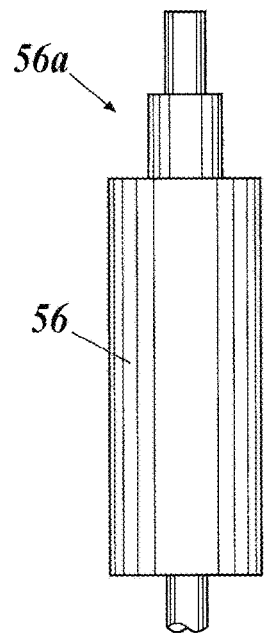
FIG. 5A is a diagram showing an emitting switch of a radiation generating apparatus.
Figure 5B:
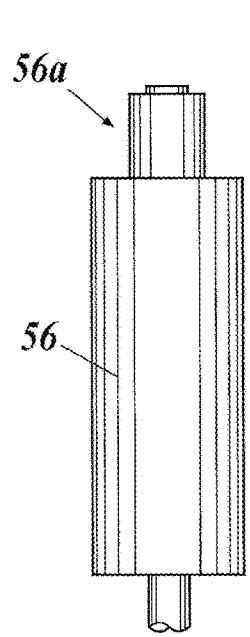
FIG. 5B is a diagram showing a button of the emitting switch of the radiation generating apparatus half pushed.
Figure 5C:
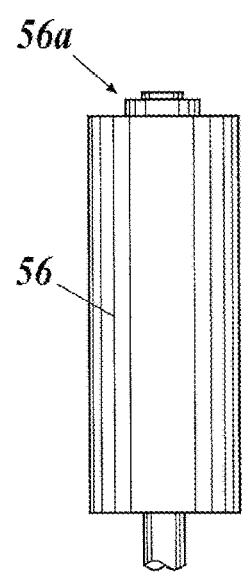
FIG. 5C is a diagram showing a button of the emitting switch of the radiation generating apparatus fully pushed.

As shown in FIG. 5A, a button 56a is provided in the emitting switch 56, when the user such as the radiology technician, etc. performs a first operation (half push) on the button 56a of the emitting switch 56 as shown in FIG. 5B, the radiation irradiating apparatus 52 starts. As shown in FIG. 5C, when the user performs the second operation on the button 56a of the emitting switch 56 (full push), the radiation irradiating apparatus 52 irradiates radiation. The irradiation of radiation from the radiation irradiating apparatus 52 is described later.

[Portable Radiation Image Capturing Apparatus]

Figure 6:
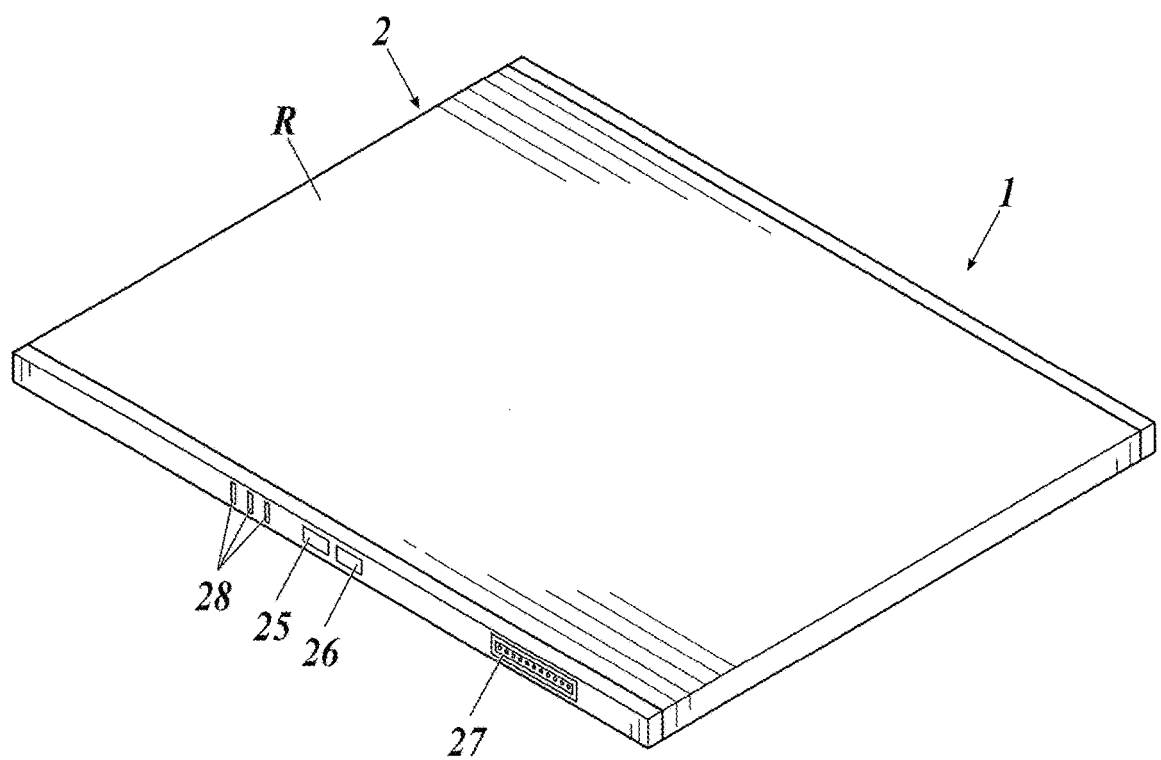
FIG. 6 is a perspective view showing an outer appearance of a portable radiation image capturing apparatus.

Here, before describing the console C, the portable radiation image capturing apparatus 1 used in the radiation image capturing system is described. Below, the portable radiation image capturing apparatus is simply referred to as the radiation image capturing apparatus. FIG. 6 is a perspective view showing the outer appearance of the radiation image capturing apparatus.

According to the present embodiment, the radiation image capturing apparatus 1 includes a case 2 with a later described radiation detecting element 7, etc. stored inside, and a power source switch 25, a switching switch 26, the above-described connector 27, and an indicator 28 are provided on one side of the case 2. Although illustration is omitted, according to the present embodiment, an antenna 29 (see later described FIG. 7) for wireless communication with external devices or systems is provided on the side opposite of the case 2. The radiation image capturing apparatus 1 uses the antenna 29 when communicating wirelessly with external devices or systems. When wired communication is performed with external devices or systems, a cable (not shown) is connected to the connector 27 for communication.

Figure 7:
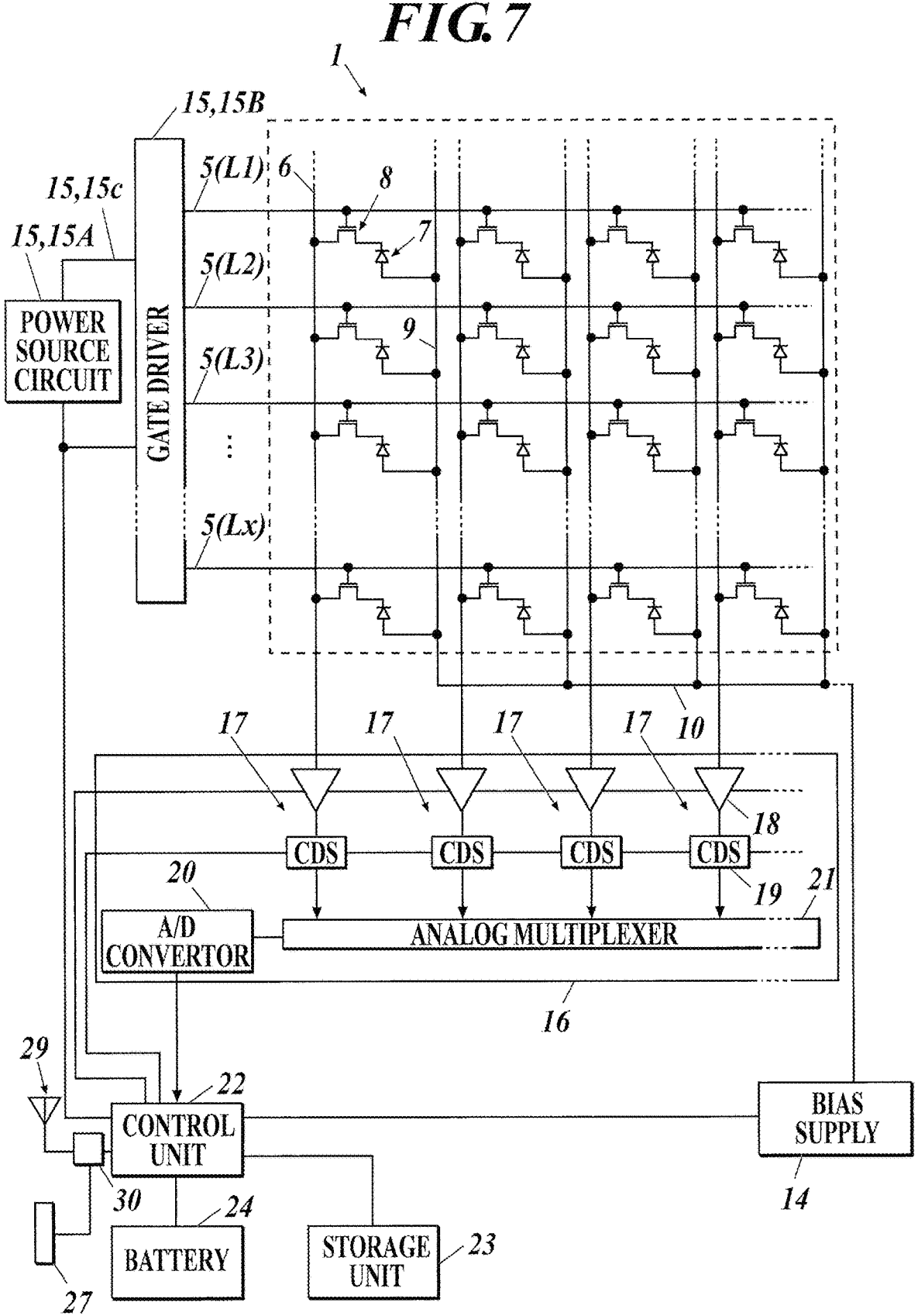
FIG. 7 is a block diagram showing an equivalent circuit of a portable radiation image capturing apparatus.

FIG. 7 is a block diagram showing an equivalent circuit of the radiation image capturing apparatus. As shown in FIG. 7, a plurality of radiation detecting elements 7 are arrayed two-dimensionally (matrix shape) on a sensor substrate (not shown) in the radiation image capturing apparatus 1. Each radiation detecting element 7 generates charge according to the amount of irradiated radiation. A bias line 9 is connected to each radiation detecting element 7, and the bias line 9 is connected to a connecting line 10. The connecting line 10 is connected to a bias supply 14, and a reverse bias voltage can be applied to each radiation detecting element 7 from the bias supply 14 through the bias line 9, etc.

A thin film transistor (TFT) 8 is connected to each radiation detecting element 7 as a switch element, and the TFT 8 is connected to the signal line 6. In a scanning driving unit 15, on voltage and off voltage supplied from a power source circuit 15a through a line 15c are switched at a gate driver 15b and are applied to each line L1 to Lx of the scanning line 5. Each TFT 8 is turned on when an on voltage is applied through the scanning line 5, and the charge accumulated in the radiation detecting element 7 is released in the signal line 6. Each TFT 8 is turned off when an off voltage is applied through the scanning line 5, and the conduction between the radiation detecting element 7 and the signal line 6 is cut so that the charge generated in the radiation detecting element 7 is accumulated in the radiation detecting element 7.

A plurality of readout circuits 17 are provided in a readout IC 16, and a signal line 6 is connected to each readout circuit 17. In processing of generating the image data D, when charge is released from the radiation detecting element 7, the charge flows into the readout circuit 17 through the signal line 6 and a voltage value according to the amount of charge flown in is output from an amplifying circuit 18. The correlated double sampling circuit 19 (described as "CDS" in FIG. 7) reads out the voltage value output from the amplifying circuit 18 as the image data D with an analog value and outputs the image data D to the downstream side. The output image data D is sequentially transmitted to an A/D convertor 20 through an analog multiplexer 21. The image data D is sequentially converted to a digital value in the A/D converter 20. The image data D is output to the storage unit 23 and sequentially stored.

The control unit 22 includes a computer in which a CPU (Central Processing Unit), a ROM (Read Only Memory), a RAM (Random Access Memory), an input/output interface, etc. (all not shown) are connected by a bus, a FPGA (Field Programmable Gate Array), or the like. A dedicated control circuit can also be configured. A storage unit 23 including a SRAM (Static RAM) and a SDRAM (Synchronous DRAM), etc. is connected to the control unit 22. A communication unit 30 which communicates by a wired or wireless format with external devices or systems through the antenna 29 or the connector 27 is connected to the control unit 22. A battery 24, etc. which supplies power necessary for each functional unit such as the scanning driving unit 15, the readout circuit 17, the storage unit 23, the bias supply 14, etc. is connected to the control unit 22.

The radiation image capturing apparatus 1 according to the present embodiment can be used for capturing loaded on a bucky apparatus 51. Although illustration is omitted, the radiation image capturing apparatus 1 can also be used for capturing independently without loading on the bucky apparatus 51. For example, the radiation image capturing apparatus 1 can be placed against the body of the patient who is the subject or inserted between the patient and the bed.

As described above, according to the present embodiment, it is assumed that the radiation image capturing apparatus 1 is used for capturing loaded on the bucky apparatus 51, in which CR cassettes are loaded, already provided in the facility. Therefore, the radiation image capturing apparatus 1 is formed in a size conforming to the CR cassette which is a JIS standard size for a conventional screen/film cassette (JIS Z 4905, corresponding to international standard IEC 60406). However, the present invention can also be applied when the radiation image capturing apparatus 1 is not formed in this size.

[Power Consumption Mode of Radiation Image Capturing Apparatus]

As described later, according to the present embodiment, the control unit 22 switches power consumption modes of the radiation image capturing apparatus 1 between at least a capturing possible mode (also called a wake up mode) in which power is provided to each functional unit including the scanning driving unit 15 and the readout circuit 17 and capturing is possible or a power save mode (also called a sleep mode) in which power consumption is smaller than the capturing possible mode and capturing cannot be performed.

According to the present embodiment, the radiation image capturing apparatus 1 automatically switches the power consumption mode from the capturing possible mode to the power save mode when, for example, the next capturing is not performed even if a predetermined amount of time passes after capturing ends. Moreover, the radiation image capturing apparatus 1 switches the power consumption mode between the capturing possible mode and the power save mode when a later described switching signal is transmitted from the console C or the user such as the radiology technician, etc. operates the switching switch 26 (see FIG. 6).

[Processing Performed in Radiation Image Capturing Apparatus]

Next, processing performed in the radiation image capturing apparatus 1 in capturing (simple capturing and long length capturing) is described. Here, processing performed in the radiation image capturing apparatus 1 is different depending on whether capturing is performed while linking the radiation image capturing apparatus 1 and the radiation irradiating apparatus 52 by transmitting and receiving signals (the capturing method referred to as linking method) or capturing is performed without transmitting and receiving signals between the radiation image capturing apparatus 1 and the radiation irradiating apparatus 52 (the capturing method referred to as non-linking method). Each method is described briefly.

[Processing in Linking Method]

Figure 8:
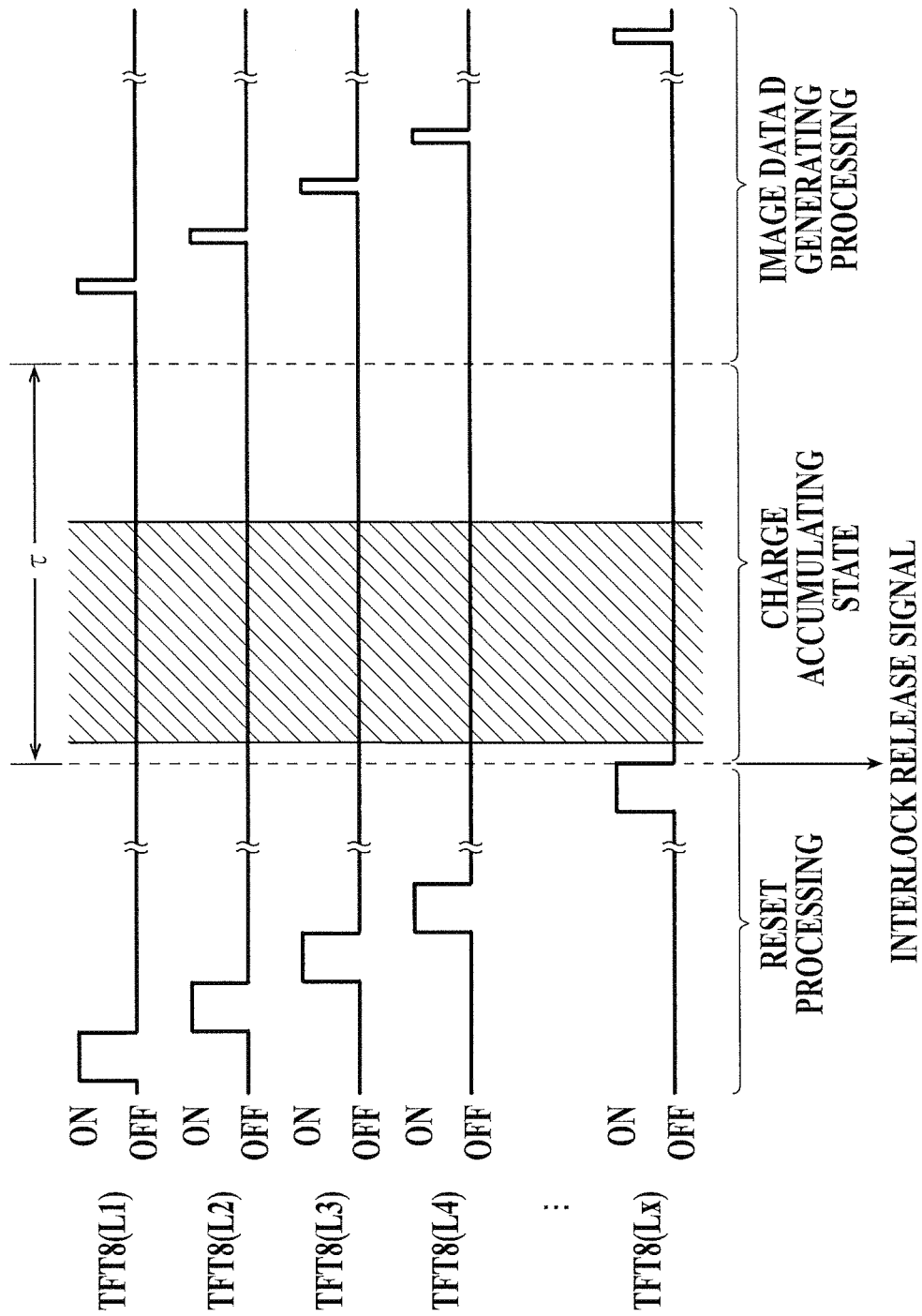
FIG. 8 is a timing chart describing timing of applying on voltage to each scanning line when capturing is performed in a linking method.

In a linking method, for example, as shown in the left side portion of FIG. 8, the radiation image capturing apparatus 1 performs reset processing of each radiation detecting element 7, in which on voltage is sequentially applied to each line L1 to Lx of the scanning line 5 from the gate driver 15b (see FIG. 7), each TFT 8 is sequentially turned on, and the charge remaining in each radiation detecting element 7 is removed.

As described above, the emitting switch 56 (see FIG. 1) is operated by the user such as the radiology technician, etc., and when the second operation, in other words, full push is performed on the emitting switch 56, the irradiating start signal is transmitted from the radiation irradiating apparatus 52 to the radiation image capturing apparatus 1. When the irradiating start signal is received, as shown in FIG. 8, the radiation image capturing apparatus 1 ends the reset processing when the on voltage is applied to the last line Lx of the scanning line 5 and the reset processing of each radiation detecting element 7 is performed.

Then, the radiation image capturing apparatus 1 applies off voltage to each line L1 to Lx of the scanning line 5 from the gate driver 15b to turn off each TFT 8, and advances to the charge accumulating state in which the charge generated in each radiation detecting element 7 by the irradiation of radiation is accumulated in each radiation detecting element 7. At the same time, an interlock release signal is transmitted to the radiation irradiating apparatus 52. The radiation irradiating apparatus 52 irradiates radiation when the interlock release signal is received. The diagonal line portion shown in FIG. 8 represents the term that the radiation is irradiated from the radiation irradiating apparatus 52.

When a predetermined charging time τ passes after advancing to the charge accumulating state, as shown in the right side portion of FIG. 8, the radiation image capturing apparatus 1 sequentially applies on voltage to each line L1 to Lx of the scanning line 5 from the gate driver 15b and the image data D is read out from each radiation detecting element 7 to perform processing of generating the image data D.

[Processing in Non-Linking Method]

On the other hand, in the non-linking method, as described above, the signal is not transmitted and received between the radiation image capturing apparatus 1 and the radiation irradiating apparatus 52. Therefore, the radiation image capturing apparatus 1 itself needs to detect that the radiation is irradiated from the radiation irradiating apparatus 52. As a method for the radiation image capturing apparatus 1 to detect irradiation of radiation, for example, methods as described in the following documents such as Japanese Patent Application Laid-Open Publication No. 2009-219538, WO 2011/135917, WO 2011/152093 can be employed. See above documents for details.

Described below is processing performed in the radiation image capturing apparatus 1 in the non-linking method. According to WO 2011/135917, the radiation image capturing apparatus 1 detects the start of irradiation of radiation based on the leak data dleak and the value calculated from the leak data dleak. The off voltage is applied to each line L1 to Lx of the scanning line 5 from the gate driver 15b, and the charge which leaks from each radiation detecting element 7 through each TFT 8 in the off state to the signal line 6 is read out with the readout circuit 17. The read out data is the leak data dleak. When the radiation is irradiated on the radiation image capturing apparatus 1, the increase of the value of the readout leak data dleak can be used to detect the start of irradiation of radiation.

As described above, the leak data dleak is data read out when each TFT 8 is in an off state. Dark charge (also called dark current) continues to accumulate in the radiation detecting element 7 when each TFT 8 remains in the off state. Therefore, as shown in the left side portion of FIG. 9, when the readout processing (see L in FIG. 9) of the leak data dleak is performed, on voltage is sequentially applied on each line L1 to Lx of the scanning line 5 from the gate driver 15b to perform reset processing (see R in FIG. 9) of each radiation detecting element 7 alternately with the readout processing.

When the user such as the radiology technician, etc. operates the emitting switch 56 and radiation is irradiated from the radiation irradiating apparatus 52, the radiation image capturing apparatus 1 detects start of irradiation of radiation based on the leak data dleak, etc. read out by readout processing of leak data dleak of a certain turn (see "detect" in FIG. 9).

Then, when the start of irradiation of radiation is detected, the radiation image capturing apparatus 1 applies off voltage to each line L1 to Lx of the scanning line 5 from the gate driver 15b and advances to the charge accumulating state. After advancing to the charge accumulating state, when the predetermined accumulating time τ passes, as shown in the right side portion of FIG. 9, on voltage is sequentially applied to each line L1 to Lx of the scanning line 5 from the gate driver 15b and the image data D is read out from each radiation detecting element 7 as described above. With this, the generating processing of the image data D is performed.

FIG. 9 shows generating processing of image data D in which, applying on voltage starts from the scanning line 5 (line L5 of scanning line 5 in FIG. 9) on which on voltage is applied next after the scanning line 5 (line L4 of scanning line 5 in FIG. 9) on which on voltage is applied for reset processing (R) directly before the read out processing (L) of leak data dleak detecting the start of irradiation of radiation. Alternatively, similar to the linking method (see FIG. 8), for example, on voltage can be sequentially applied from the first line L1 of the scanning line 5 to perform generating processing of the image data D.

[Processing after Generating Processing of Image Data]

According to the present embodiment, in both the linking method and the non-linking method, when the generating processing of the image data D is performed as described above, the radiation image capturing apparatus 1 extracts the preview image data Dp at a predetermined percentage from the readout image data D, and transfers the extracted preview image data Dp to the console C. As described later, according to the console C, the preview image is generated based on the preview image data Dp transferred from the radiation image capturing apparatus 1, and the preview image is displayed on the display unit Ca.

When the preview image data Dp is extracted and transferred to the console C, at the same time, the radiation image capturing apparatus 1 starts the readout processing of the offset data O as shown in FIG. 10. FIG. 10 describes readout processing of the offset data O in the linking method shown in FIG. 8.

In other words, when the generating processing of the image data D, and the extracting and transferring processing of the preview image data Dp is performed, then, as shown in the left side portion of FIG. 10, the radiation image capturing apparatus 1 advances to the charge accumulating state after the reset processing of each radiation detecting element 7 for one frame or a predetermined number of frames. Then, in a state in which the radiation is not irradiated to the radiation image capturing apparatus 1, when accumulating time r set at the same amount of time as the above accumulating time r passes, as shown in the right side portion of FIG. 10, on voltage is sequentially applied to each line L1 to Lx of the scanning line 5 from the gate driver 15, and offset data O is read out from each radiation detecting element 7 similar to the generating processing of the image data D.

As described above, other than the radiation not being irradiated to the radiation image capturing apparatus 1, the processing sequence the same as the processing sequence up to the generating processing of the image data D is repeated to perform the readout processing of the offset data O. Although illustration is omitted, in the non-linking method shown in FIG. 9 also, the processing sequence shown in FIG. 9 is repeated and the readout processing of the offset data O is performed. The readout processing of the offset data O can be performed before capturing.

When the offset data O is read out as described above, according to the present embodiment, when there is a transfer request from the console C, the radiation image capturing apparatus 1 transfers the image data D other than the preview image data Dp and the offset data O read out from each radiation detecting element 7 to the console C. The image data D and the offset data O can be immediately automatically transferred to the console C when the readout processing of the offset data O ends.

[Configuration of Console]

As shown in FIG. 1 and FIG. 2, according to the present embodiment, the console C including a computer, etc. is provided in the front room Rb (FIG. 1) or outside the capturing room (FIG. 2). The console C can be provided in a suitable location.

A display unit Ca composed of a CRT (Cathode Ray Tube) or an LCD (Liquid Crystal Display) is provided in the console C, and includes an input unit such as a mouse or keyboard which is not shown. A storage unit Cb composed of the HDD (Hard Disk Drive) is connected to or included in the console C. Although illustration is omitted, HIS (Hospital Information System), RIS (Radiology Information System), PACS (Picture Archiving and Communication System) are connected to the console C through the network N, etc.

[Associating Console and Capturing Room]

There is no particular problem in the radiation image capturing system 50 in which the capturing room Ra and the console C are associated to each other in advance one to one as shown in FIG. 1. However, as shown in FIG. 2, in an example in which a plurality of capturing rooms Ra (Ra1 to Ra3) are associated to a plurality of consoles C through the network N, etc., there is a possibility that even if the user such as the radiology technician, etc. performs a later described determination processing on the console C for the image data D captured in the capturing room Ra1, the image data D may be transferred to another console C and the processing may not be reliably performed.

As shown in FIG. 2, in most configurations of the radiation image capturing system 50 in which a plurality of capturing rooms Ra and a plurality of consoles C are associated, the user such as the radiology technician, etc. usually performs processing to specify (or direct) the capturing room Ra to be used on one console C before capturing. When the capturing room Ra is specified on a certain console C, the image data D, etc. is not transferred to the other consoles C from the specified capturing room Ra, and the image data D is transferred to only the certain console C. With this, the console C is associated with the capturing room Ra.

For example, in this case, when the capturing room Ra1 is specified as the capturing room to be used on the console C1, if the radiation image capturing apparatus 1 in the capturing room Ra1 is brought out and inserted in the cradle 55 of the capturing room Ra2, since the capturing room Ra2 is not associated with the console C1, the radiation image capturing apparatus 1 cannot be controlled by the console C1. Alternatively, if the radiation image capturing apparatus 1 is brought into the capturing room Ra1 and inserted in the cradle 55 from another capturing room Ra or storage room, etc., the radiation image capturing apparatus 1 can be controlled by the console C1.

[Processing in Console]

Next, the processing in capturing in the console C is described. The operation of the radiation image capturing system 50 according to the present embodiment is also described.

When the console C is operated by the user such as the radiology technician, etc., the capturing order information regarding the radiation image capturing to be performed is obtained from the HIS or the RIS. According to the present embodiment, as illustrated in the example of FIG. 11, the capturing order information includes, patient information such as "patient ID" P2, "patient name" P3, "sex" P4, "age" P5, and "department" P6, and capturing condition such as "capturing site" P7, "capturing direction" P8, and "posture" P9. The "capturing order ID" P1 is automatically assigned to each piece of capturing order information in the order that the capturing order is received.

When the console C obtains capturing order information, as shown in FIG. 12, a list of the capturing order information is displayed in the selection screen H1 on the display unit Ca. In the selection screen H1, a capturing order information display column h11 is provided to display a list of the capturing order information and a selection button h12 is provided on the left side of the capturing order information display column h11 to select the capturing order information. An enter button h13 and a return button h14 are provided below the capturing order information display column h11.

When the user clicks the select button h12 to select the capturing order information, and clicks the enter button h13, the console C displays the screen H2 as shown in FIG. 13 on the display unit Ca. FIG. 13 shows an example in which 4 pieces of capturing order information regarding the patient "A" are selected from the capturing order information shown in FIG. 12. In the example of the screen H2 shown in FIG. 13, by clicking a "+" button or a "−" button of each item on a display Ia for setting the irradiating condition on the right side of the screen, the irradiating condition such as tube voltage, tube current, irradiating time, etc. of the radiation irradiating apparatus 52 can be changed and set.

On the left side of the screen H2, the capturing site P7 (see FIG. 11 and FIG. 12) specified by the capturing order information corresponding to an icon I displayed with focus as described later is displayed on a human body model Ib shown so that the user such as the radiology technician, etc. is able to understand at a glance.

Each icon I corresponding to each selected capturing order information is displayed in the center portion of the screen H2. The icon I (icon I2 in FIG. 13) corresponding to the capturing to be performed is displayed with focus so as to stand out. When the user wants to perform capturing based on capturing order information different from the capturing order information corresponding to the icon I displayed with focus, the user can click on another icon I corresponding to the different capturing order information and make a selection to change the icon I displayed with focus.

According to the example shown in FIG. 13, each icon I displays an outline drawing showing modality of the bucky apparatus 51A for long length capturing or the bucky apparatus 51B, 51C for standing position capturing or lying position capturing used in simple capturing and the tube voltage, the tube current, the irradiating time, etc. which are set.

It is possible to be able to specify in advance whether the capturing is long length capturing or simple capturing as the capturing condition in the capturing order information. In this case, the console C determines the outline drawing displayed in each icon I according to the capturing method specified in the capturing order information, in other words, whether the long length capturing or the simple capturing is specified.

[Determination of Long Length Capturing or Simple Capturing by Console]

According to the present embodiment, it is possible to not specify whether the capturing is performed by long length capturing or simple capturing in the capturing order information (see FIG. 11). For example, as shown in FIG. 11, even if "entire lower extremity" is specified as the capturing site P7, if the subject is an adult, long length capturing needs to be performed, but if the subject is an infant, the "entire lower extremity" can be captured by simple capturing using one radiation image capturing apparatus 1. In other words, even if the "entire lower extremity" is specified as the capturing site P7 on the capturing order information, long length capturing is not always performed.

When long length capturing or simple capturing is not specified on the capturing order information, the console C is configured to judge whether the capturing is performed by long length capturing or simple capturing based on the capturing order information. In this case, the console C is configured to judge whether the capturing is performed by long length capturing or simple capturing based on age P5 of the patient who is the subject or capturing site P7.

However, the judgment of the console C and the judgment by the user such as the radiology technician, etc. may not always match. Therefore, for example, when the console C judges to perform the capturing by long length capturing based on the age P5 of the patient, the capturing site P7, etc. specified in the capturing order information as described above, the above judgment can be displayed on the display unit Ca, and the judgment of the user can be consulted by displaying a button icon showing "YES" or "NO" (not shown).

[Selection of Radiation Image Capturing Apparatus to be Used]

Figure 14:
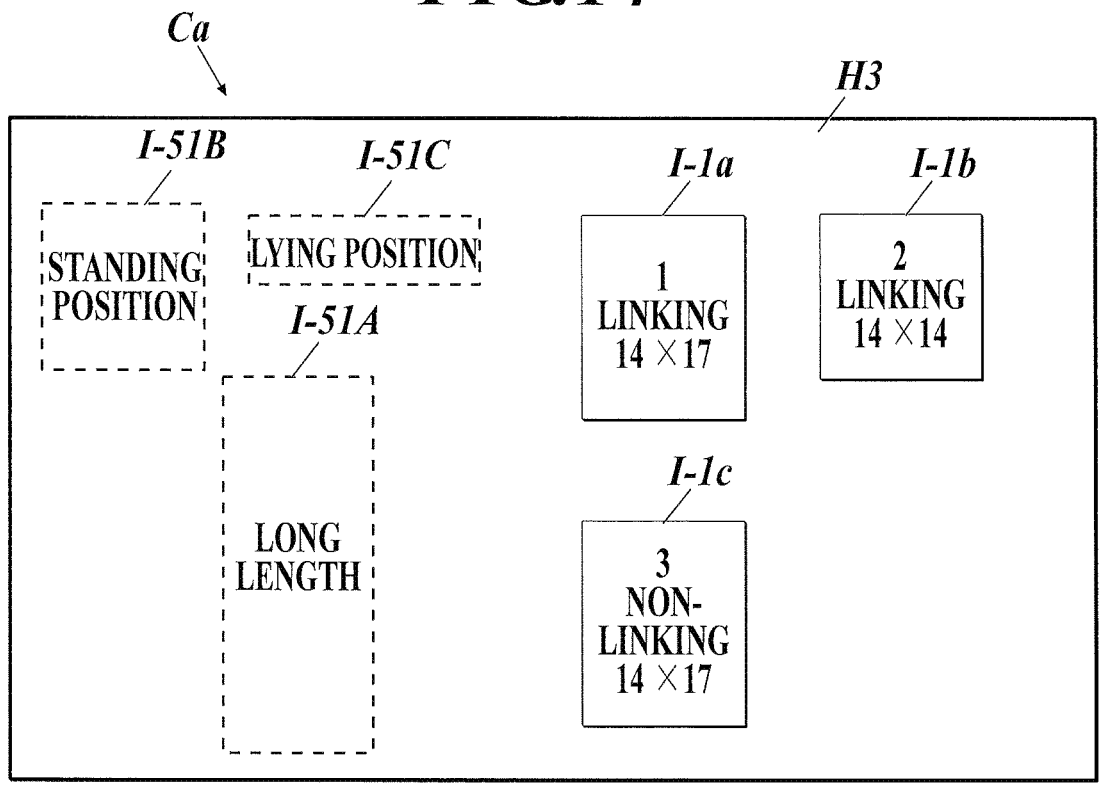
FIG. 14 is a diagram showing an example of a selection screen displaying an icon corresponding to the radiation image capturing apparatus in a capturing room.

Based on the operation by the user such as the radiology technician, etc., the console C displays a selection screen H3 of the radiation image capturing apparatus 1 as shown in FIG. 14 on the display unit Ca. The icons I corresponding to the radiation image capturing apparatuses 1 in the capturing room Ra is displayed on the selection screen H3 (according to the example of FIG. 14, I-1a, I-1b, I-1c).

According to the present embodiment, when the radiation image capturing apparatus 1 is brought into the capturing room Ra, and the radiation image capturing apparatus 1 is inserted in the cradle 55 or the tag of the radiation image capturing apparatus 1 is read by the tag reader 60, the cassette ID which is the identification information of the radiation image capturing apparatus 1 is transmitted from the above detecting units through the repeater 54 to the console C. Therefore, the console C is able to store the above in the predetermined storage region of the storage unit Cb so as to be able to recognize and manage which radiation image capturing apparatus 1 is in the capturing room Ra.

Then, when the predetermined operation on the screen H2 is performed by the user as described above, the cassette ID of the radiation image capturing apparatus 1 in the capturing room Ra is read from the storage region of the storage unit Cb and the icon I corresponding to the radiation image capturing apparatus 1 in the capturing room Ra is displayed on the selection screen H3.

According to the present embodiment, for example, as shown in FIG. 14, when the icon I corresponding to the radiation image capturing apparatus 1 is displayed, the console C displays whether the radiation image capturing apparatus 1 is an apparatus which performs capturing by the above-described linking method or non-linking method on the icon I. When it is possible to perform capturing by either the linking method or the non-linking method, this is notified by displaying, for example, "linking/non-linking". The size (14×17 inches, etc.) of the radiation image capturing apparatus 1 is also displayed in the icon I.

Below, the radiation image capturing apparatus 1 which is a type performing capturing with a linking method is referred to as linking method radiation image capturing apparatus 1, and the radiation image capturing apparatus 1 which is a type performing capturing with a non-linking method is referred to as non-linking method radiation image capturing apparatus 1. As described above, in addition to the capturing method (linking method or non-linking method) and size, for example, the resolution, scintillator type, etc. of the radiation image capturing apparatus 1 can also be displayed in the icon I, and the content to be displayed can be suitably determined.

Although illustration is omitted, instead of or in addition to displaying the capturing method, size, etc. of the radiation image capturing apparatus 1 as characters, etc. in the icon I as shown in FIG. 14, it is possible to display the above by color or design. In other words, for example, the linking method radiation image capturing apparatus 1 is displayed with blue, the non-linking method radiation image capturing apparatus 1 can be displayed with red, and each of the following sizes of 14×17 inches, 14×14 inches, 17×17 inches, etc. is displayed by design such as rectangle (solid colored), stripe, dots, etc.

As described above, when the color or design representing the capturing method and the size of the radiation image capturing apparatus 1 are displayed in the icon I corresponding to the radiation image capturing apparatus, compared to when only the characters are displayed, the user such as the radiology technician, etc. is able to understand the capturing method and the size of the radiation image capturing apparatus 1 at a glance. Therefore, the possibility that the user selects the wrong capturing method or the size of the radiation image capturing apparatus 1 can be decreased. Since the same color, design, etc. is displayed in a predetermined position such as the side face of the radiation image capturing apparatus 1, etc. (see FIG. 6), the user such as the radiology technician, etc. is able to recognize the capturing method, size, etc. of the radiation image capturing apparatus 1 by color, design, etc., and the possibility that the capturing method, size, etc. of the radiation image capturing apparatus 1 is mistaken and the wrong radiation image capturing apparatus 1 being used can be reduced.

According to the present embodiment, the console C displays the icon I corresponding to the modality in the capturing room Ra on the selection screen H3. FIG. 14 shows an example in which the bucky apparatuses MA, MB, and MC for long length capturing, simple capturing, and lying position capturing are provided in the capturing room Ra as the modality. Alternatively, for example, when only the bucky apparatus MA for long length capturing is provided, only the icon I-MA corresponding to the bucky apparatus MA for long length capturing is displayed.

Figure 15:
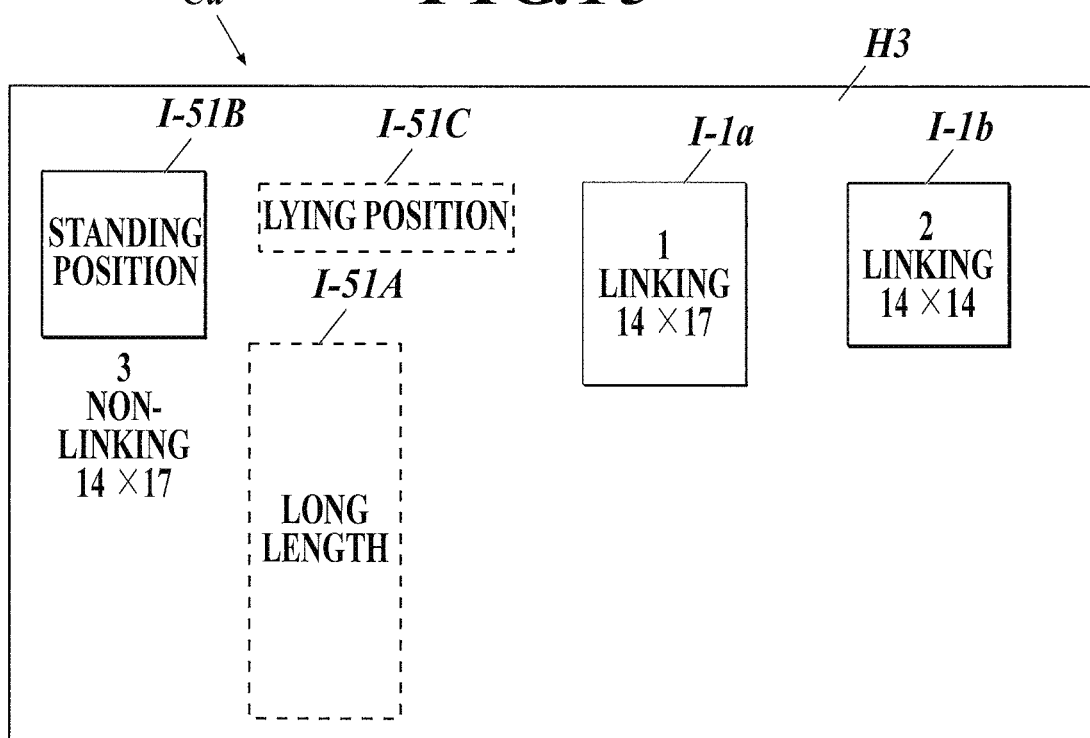
FIG. 15 is a diagram showing an example of display of an icon corresponding to a bucky apparatus in which the radiation image capturing apparatus is loaded displayed on the selection screen shown in FIG. 14.

Here, when the radiation image capturing apparatus 1 is not loaded, for example, the frame of the icon I corresponding to the bucky apparatuses 51 is displayed with broken lines as shown in FIG. 14. When the radiation image capturing apparatus 1 is loaded, for example, the frame is displayed with solid lines as shown in FIG. 15 and the capturing method and the size of the loaded radiation image capturing apparatus 1 is displayed nearby.

According to the present embodiment, the user such as the radiology technician, etc. is able to select the radiation image capturing apparatus 1 to be used in the capturing to be performed, in other words, the radiation image capturing apparatus 1 used in the capturing corresponding to the icon I (icon I2 shown in FIG. 13) displayed with focus as shown in FIG. 13 by clicking the icon I corresponding to the radiation image capturing apparatus 1 on the selection screen H3.

Figure 16:
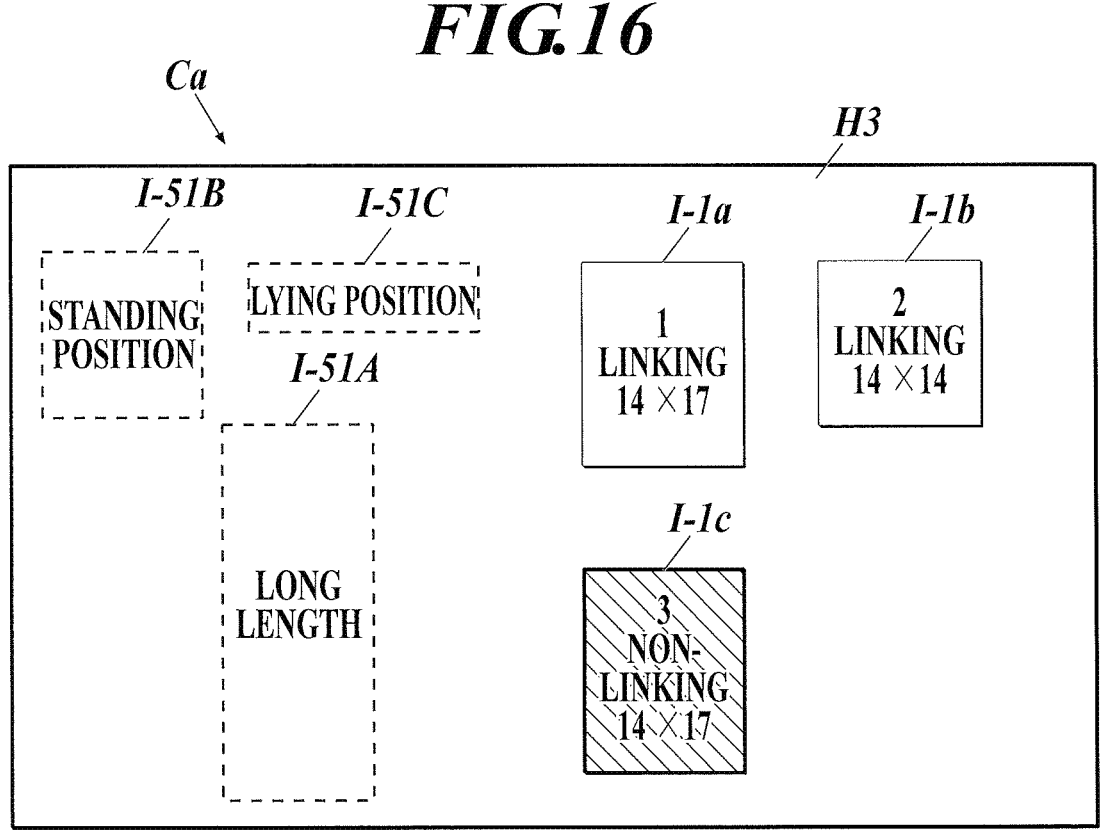
FIG. 16 is a diagram showing an example of display when the icon corresponding to the radiation image capturing apparatus is selected on the selection screen shown in FIG. 14.

Then, when the icon I corresponding to the radiation image capturing apparatus 1 is selected on the selection screen H3, for example, as shown in FIG. 16, the selected icon I is displayed differently from the display of other icons I such as with color (see icon I-1c displayed with diagonal lines in FIG. 16). Such display shows that the icon I is selected.

The console C is able to control the radiation image capturing apparatus 1 to switch the above-described power consumption mode. In other words, when the icon I is selected on the selection screen H3, and the radiation image capturing apparatus 1 is selected, the console C transmits a switching signal to the selected radiation image capturing apparatus 1, and the power consumption mode of the radiation image capturing apparatus 1 is switched from power save mode to capturing possible mode.

In other words, according to the present embodiment, when the icon I corresponding to the radiation image capturing apparatus 1 is selected on the selection screen H3, the console C changes the state of display of the icon I to the state of display showing that the icon I is selected and the icon I is displayed as described above. Moreover, the console C transmits a switching signal to the radiation image capturing apparatus 1 corresponding to the selected icon I, and switches the power consumption mode of the radiation image capturing apparatus 1 from the power save mode to the capturing possible mode.

According to the present embodiment, when it is judged that the capturing is simple capturing based on the capturing order information regarding the capturing to be performed, the console C controls only one radiation image capturing apparatus 1 among the radiation image capturing apparatuses 1 in the capturing room Ra to be the capturing possible mode.

In other words, when it is judged that the capturing to be performed is simple capturing, and the icon I corresponding to the radiation image capturing apparatus 1 is selected on the selection screen H3 by the user such as the radiology technician, etc., the switching signal is transmitted to the radiation image capturing apparatus 1 and the power consumption mode is switched to the capturing possible mode. Here, when there is another radiation image capturing apparatus 1 with the power consumption mode set to the capturing possible mode, a signal to instruct the other radiation image capturing apparatus 1 to switch the power consumption mode to the power save mode is transmitted so that the power consumption mode of the other radiation image capturing apparatus 1 is switched from the capturing possible mode to the power save mode.

As described above, when the user such as the radiology technician, etc., operates the switching switch 26 (see FIG. 6) of the radiation image capturing apparatus 1, the power consumption mode of the radiation image capturing apparatus 1 can be switched from the power save mode to the capturing possible mode. When the user switches the power consumption mode of the radiation image capturing apparatus 1 to the capturing possible mode, it is assumed that the user desires to perform capturing using the radiation image capturing apparatus 1.

Therefore, for example, when the user such as the radiology technician, etc., operates the switching switch 26 of the radiation image capturing apparatus 1 in the capturing room Ra and switches the power consumption mode to capturing possible mode, the console C performs processing similar to when the icon I corresponding to the radiation image capturing apparatus 1 is selected on the selection screen H3. When the power consumption mode of the other radiation image capturing apparatus 1 is in a capturing possible mode, similar to the above, the power consumption mode of the radiation image capturing apparatus 1 is switched to the power save mode.

According to the present embodiment, as described above, when it is judged that the capturing to be performed is simple capturing, the console C allows only one of the radiation image capturing apparatuses 1 in the capturing room Ra to advance to the capturing possible state (in other words, capturing possible mode).

According to the above configuration, when the capturing to be performed is simple capturing, by allowing only one radiation image capturing apparatus 1 in the capturing room Ra to advance to the capturing possible state (capturing possible mode), and setting the electric consumption mode of the other radiation image capturing apparatuses 1 to the power save mode, the following advantageous effects can be achieved.

When the power consumption mode of the other linking method radiation image capturing apparatus 1 is in the capturing possible mode, the other radiation image capturing apparatus 1 which is not used in the capturing may return an interlock release signal to the radiation irradiating apparatus 52 transmitting the irradiating start signal in capturing. Then, the irradiation may be irradiated from the radiation irradiating apparatus 52 even when the radiation image capturing apparatus 1 to be used in the capturing has not yet advanced to the charge accumulating state. According to the present embodiment, it is possible to accurately prevent the above situation.

When the power consumption mode of the other non-linking method radiation image capturing apparatus 1 is in the capturing possible mode, the other radiation image capturing apparatus 1 may detect the start of irradiation of radiation when the irradiation of the radiation from the radiation irradiating apparatus 52 starts. After advancing to the charge accumulating state, generating processing of the image data D may be performed, and the preview image data Dp, the image data D, etc. may be transferred to the console C. After capturing, the preview image data Dp, the image data D, etc. may be transferred to the console C from the plurality of radiation image capturing apparatuses 1, which are the radiation image capturing apparatus 1 used in the capturing and the radiation image capturing apparatus 1 not used in the capturing. According to the present embodiment, it is possible to accurately prevent the above situation.

Therefore, according to the above configuration, it is possible to accurately prevent confusion as described above from occurring when the simple capturing is performed, and simple capturing can be accurately performed. Regardless of whether the linking method radiation image capturing apparatus 1 or the non-linking method radiation image capturing apparatus 1 is used, it is possible to accurately prevent wasting power of the radiation image capturing apparatus 1 by switching the power consumption mode of the radiation image capturing apparatus 1 not used in the capturing to the power save mode.

Alternatively, when the capturing to be performed is long length capturing, it is necessary for the power consumption mode of the plurality of radiation image capturing apparatuses 1 used in the long length capturing to be in the capturing possible mode at the same time. Therefore, when the capturing to be performed is judged to be long length capturing, the console C allows the icons I corresponding to the plurality of radiation image capturing apparatuses 1 in the capturing room Ra to be selected on the selection screen H3, and allows the plurality of radiation image capturing apparatuses 1 to advance to the capturing possible state (in other words, capturing possible mode).

According to the above configuration, when the capturing to be performed is long length capturing, the plurality of radiation image capturing apparatuses 1 in the capturing room Ra are allowed to advance to the capturing possible state (capturing possible mode), and the long length capturing can be accurately performed.

[Effect]

As described above, according to the radiation image capturing system 50 of the present embodiment, when the console C judges that the capturing is long length capturing based on the capturing order information, the console C allows the plurality of radiation image capturing apparatuses 1 in the capturing room Ra to advance to the capturing possible state (in other words, capturing possible mode). When the console C judges that the capturing is not long length capturing (in other words, it is simple capturing), the console C allows only one of the radiation image capturing apparatuses 1 in the capturing room Ra to advance to the capturing possible state. Therefore, the capturing can be accurately performed regardless of whether the capturing to be performed is the simple capturing or the long length capturing.

As shown in FIG. 2, when the radiation image capturing system 50 is configured so that the plurality of capturing rooms Ra (Ra1 to Ra3) are associated with one or a plurality of consoles C, similarly, when the console C judges that the capturing is long length capturing based on the capturing order information, the plurality of radiation image capturing apparatuses 1 in the capturing room Ra associated with the console C is allowed to advance to the capturing possible state and when the console C judges that the capturing is not the long length capturing, only one radiation image capturing apparatus 1 in the associated capturing room Ra is allowed to advance to the capturing possible state. With this, the capturing can be accurately performed regardless of whether the capturing to be performed is the single capturing or the long length capturing.

In both the simple capturing and the long length capturing, even if the radiation image capturing apparatus 1 to be used is selected but the radiation image capturing apparatus 1 is not loaded on the suitable bucky apparatus 51, measures necessary to warn the user such as the radiology technician, etc. that the radiation image capturing apparatus 1 is not loaded on the bucky apparatus 51 are suitably taken such as a beeping sound may be generated from the console C or an alarm device, etc. (not shown) provided in the capturing room Ra.

According to the above, the power consumption mode of the radiation image capturing apparatus 1 being in the capturing possible mode is described as the state in which capturing by the radiation image capturing apparatus 1 is possible. The capturing possible state of the radiation image capturing apparatus 1 is not limited to when the power consumption mode of the radiation image capturing apparatus 1 is in the capturing possible mode. For example, the radiation image capturing apparatus 1 can be set to the capturing possible state when the power of the radiation image capturing apparatus 1 in the off state is turned on.

[Processing Thereafter in the Console]

Figure 17:
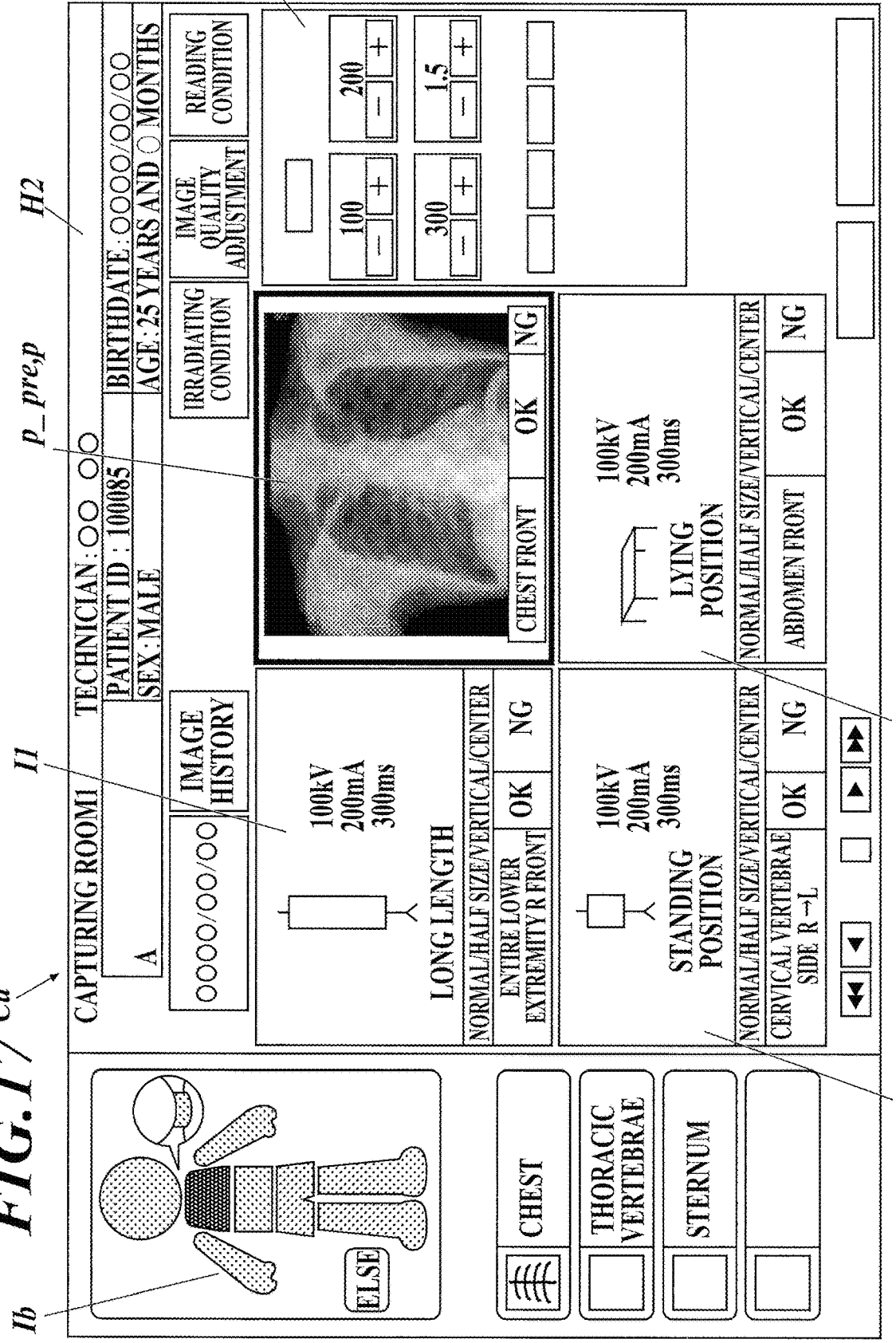
FIG. 17 is a diagram showing a preview image and a radiation image are displayed on an icon displayed with focus on the screen shown in FIG. 13.

As described above, regardless of whether the capturing is performed by the linking method or the non-linking method, the preview image data Dp is transferred from the radiation image capturing apparatus 1 to the console C when the capturing ends. Therefore, the console C performs predetermined image processing on the transferred preview image data Dp and preview image p_pre is generated. The preview image p_pre is displayed in the position of the icon I displayed with focus on the screen H2 as described in FIG. 17, in other words, the icon I (see icon I2 of FIG. 13) corresponding to the capturing order information regarding the capturing. The preview image p_pre can be displayed enlarged on the screen H2.

Similarly in simple capturing and long length capturing, as described above, when the radiation image capturing apparatus 1 is formed in the size conforming to the JIS standard size, the vertical direction and the horizontal direction of the radiation image capturing apparatus 1 when the radiation image capturing apparatus 1 is loaded on the bucky apparatus 51 may not be the correct direction and may be opposite (in other words, rotated 180°). Therefore, when the image read from the radiation image capturing apparatuses 1 is displayed as is, the preview image p_pre and the later described radiation image p may be displayed in the incorrect direction. In such case, subject site recognizing processing or display rotating processing as described in Japanese Patent No. 3731400 or Japanese Patent Application Laid-Open Publication No. 2000-157519 can be used to display the images in the correct direction (in other words, direction suitable for interpretation) or display the combined long length image in the correct direction.

When the user such as the radiology technician, etc. sees the preview image p_pre, judges that capturing needs to be performed again, and for example, the "NG" button icon of the icon I is clicked, the console C instructs the information of the preview image p_pre to be destroyed and instructs the radiation image capturing apparatus 1 to perform capturing again. The radiation image capturing apparatus 1 which receives the instruction stops the readout processing of the offset data O performed at the moment, and prepares for capturing again by, for example, performing the reset processing of the radiation detecting elements 7 again.

When the user such as the radiology technician, etc. sees the preview image p_pre and clicks the "OK" button icon of the icon I, or the "NG" button icon is not clicked within a predetermined amount of time after the console C displays the preview image p_pre, it is judged that the user approved the preview image p_pre, and the user judged that the capturing does not need to be performed again. Then, a request for transfer is made to the radiation image capturing apparatus 1.

When the radiation image capturing apparatus 1 receives the transfer request, the image data D other than the preview image data Dp and the offset data O is transferred to the console C. Then, when the image data D, the offset data O, etc. are transferred from the radiation image capturing apparatus 1 as described above, the console C subtracts the offset data O from the image data D for each radiation detecting element 7 according to the formula (1) described below and calculates the true image data D*.

$$D^* = D - O \qquad (1)$$

Then, gain correction and the defective pixel correction is performed on the calculated true image data D*, the image processing such as gradation processing according to the capturing site is performed to generate the radiation image, and the generated radiation image p is overwritten and displayed on the preview image p_pre.

After fine adjustment of the image is performed as necessary by the user who sees the radiation image p, when the "OK" button icon of the icon I is clicked and the finalizing processing is performed, the console C associates the data of the generated radiation image p with the capturing order information regarding the capturing to finalize the capturing order information, and transmits the finalized capturing order information and the radiation image p to the external system such as PACS as necessary.

Figure 18A:
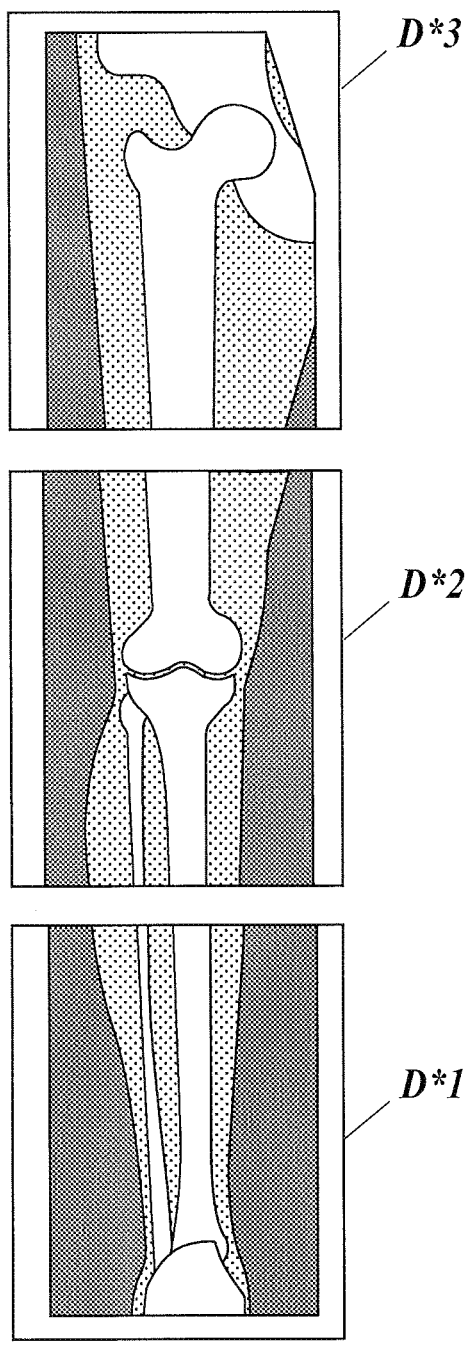
FIG. 18A is a diagram describing true image data calculated for each radiation image capturing apparatus in long length capturing.

In long length capturing, the image data D and the offset data O are transferred from the three radiation image capturing apparatuses 1 shown in FIG. 1 to the console C. Similar to the above-described simple capturing, the console C calculates the true image data D* (in other words, D*1 to D*3 in the diagram) as shown in FIG. 18A based on the image data D and the offset data O transferred from the radiation image capturing apparatuses 1. The true image data D* is referred to as simply the image data D*.

The console C positions the edges of the image data D*1 to D*3, combines the plurality of pieces of image data D*1 to D*3, and generates one piece of long length image data D*long. Here, as described above (see FIG. 1), according to the present embodiment, since the capturing can be performed by irradiating the radiation only once (in other words, one shot) from the radiation irradiating apparatus 52, the problem of body movement of the subject H does not occur. Therefore, the image data D*1 to D*3 can be accurately combined and the long length image data D*long can be generated.

Well-known methods such as methods described in Japanese Patent Application Laid-Open Publication No. 2013-154146 can be used in the positioning, combining processing, etc. of the image data D*1 to D*3. In the long length capturing also, the preview image data Dp is transferred from the radiation image capturing apparatus 1 to the console C before the image data D, etc. is transferred. Therefore, the console C performs predetermined image processing on the preview image data Dp transferred form the radiation image capturing apparatus 1 to generate the preview image p_pre and the preview image p_pre combining the above is displayed on the screen H2.

When the preview image data Dp, the image data D, etc. are transferred almost simultaneously by wireless communication from the plurality of radiation image capturing apparatuses 1, the wireless communication may interfere with each other. Therefore, for example, it is possible to transfer the data from the radiation image capturing apparatuses 1 to the console C through different channels.

Similar to the above, if the plurality of radiation image capturing apparatuses 1 are not loaded in the right direction when loaded in the long length capturing bucky apparatus 51A, the positioning of the edges of the image data D*1 to D*3 and the combining processing of the image data D*1 to D*3 cannot be suitably performed within a short amount of time. Therefore, in this case, in the long length capturing also, normally, positioning and the combining processing can be performed by using the state that the radiation is irradiated from the radiation irradiating apparatus 52 to the subject H with the irradiating field narrowed.

Specifically, since the radiation is irradiated in a state in which the irradiating field is narrowed, the radiation is not irradiated to the bottom edge portion (see FIG. 18A) of the image data D*1 generated in the radiation image capturing apparatus 1 provided in the bottom edge among the three radiation image capturing apparatuses 1 (see FIG. 1) loaded on the long length capturing bucky apparatus 51A, and the subject H is often not captured. The radiation is also not irradiated to the top edge portion of the image data D*3 generated in the radiation image capturing apparatus 1 positioned in the top edge, and the subject H is often not captured. On the other hand, in the image data D*2 generated in the radiation image capturing apparatus 1 positioned in the center, the radiation reaches the top edge portion and the bottom edge portion. Therefore, the subject H is captured.

Therefore, for example, the console C observes the profile (in other words, whether there is an edge) of the image data at the top edge portion and the bottom edge portion in the generated three pieces of image data D*1 to D*3. The image data D*2 which has gradation formed when capturing the subject H on the top edge portion and the bottom edge portion is determined to be the image data generated in the radiation image capturing apparatus 1 provided in the center among the three radiation image capturing apparatuses 1 loaded on the long length capturing bucky apparatus 51A.

Then, for example, pattern matching of the edge portion of the image data D*1 to D*3 may be performed. With the image data D*2 generated in the radiation image capturing apparatus 1 positioned in the center as the reference, the image data D*1 generated in the radiation image capturing apparatus 1 positioned in the bottom side and the image data D*3 generated in the radiation image capturing apparatus 1 positioned in the top side may be determined. Then, the positioning and the combining processing may be performed. In this case also, the combined and generated long length image data D*long may be upside down entirely. In this case, for example, it is possible to apply the above-described display rotation processing on the combined and generated one piece of long length image data D*long to display in the correct direction.

When the long length capturing is performed, if different amount of accumulating time τ (see FIG. 8 and FIG. 9) is set in the plurality of radiation image capturing apparatuses 1, after capturing, the preview image data Dp, the image data D, etc. are transferred in different timing from each radiation image capturing apparatus 1, and the processing in the console C becomes difficult to perform.

Therefore, for example, the console C is able to control the plurality of radiation image capturing apparatuses 1 used in long length capturing to transmit the information of the specific accumulating time τ and to perform processing in each radiation image capturing apparatus 1 based on the specific accumulating time τ while at least the long length capturing is performed. Alternatively, including the other radiation image capturing apparatuses 1 in the power save mode, the console C can transmit the information of the specific accumulating time τ to all of the radiation image capturing apparatuses 1, and set the specific accumulating time τ in all of the radiation image capturing apparatuses 1 at least while the long length capturing is performed. In this case, after the long length capturing, the accumulating time τ of each radiation image capturing apparatus 1 is returned to the original accumulating time τ.

Then, in the long length capturing also, similar to the simple capturing, after the user who sees the radiation image p of the long length capturing generated and displayed by the console C performs fine adjustment of the image as necessary, when the finalizing processing is performed by, for example, clicking the "OK" button icon of the icon I, the console C associates the data of the generated radiation image p of the long length capturing with the capturing order information regarding the capturing to finalize the capturing order information, and the finalized capturing order information, the radiation image p of the long length capturing, etc. are transmitted to the external system such as PACS as necessary.

[Specific Cases]

Next, specific cases which may occur when the radiation image capturing system 50 is applied are described below.

[Example when Radiation Irradiating Apparatus is Receiving Interlock Control]

Described below is an example when the radiation irradiating apparatus 52 is receiving interlock control as described above, in other words, an example in which the radiation irradiating apparatus 52 is a type in which an irradiating start signal is transmitted to the radiation image capturing apparatus 1 when the emitting switch 56 is fully pressed (see FIG. 5C), and the radiation is irradiated when the interlock release signal is received from the radiation image capturing apparatus 1.

When simple capturing is performed using the linking method radiation image capturing apparatus 1, as described above, the radiation image capturing can be performed by communicating with the signal (irradiating start signal, interlock release signal, etc.) between the radiation image capturing apparatus 1 and the radiation irradiating apparatus 52.

When the long length capturing is performed using the plurality of linking method radiation image capturing apparatuses 1, if the plurality of radiation image capturing apparatuses 1 separately transmit the interlock release signal in response to the irradiating start signal from the radiation irradiating apparatus 52, the radiation is irradiated when the radiation irradiating apparatus 52 receives the first interlock release signal. Therefore, there is a possibility that the radiation is irradiated to the radiation image capturing apparatus 1 which has not yet advanced to the charge accumulating state.

Therefore, in such situation, the radiation irradiating apparatus 52 can be set so that the radiation is irradiated when the interlock release signal is transmitted from all radiation image capturing apparatuses 1. However, in this case, it is necessary to rewrite the program of the radiation irradiating apparatus 52. Therefore, the following configuration is possible, for example, the signal communicated between the radiation irradiating apparatus 52 and each radiation image capturing apparatus 1 is repeated by the repeater 54 (see FIG. 1 and FIG. 2) and the console C, and the repeater 54 and the console C does not transmit the interlock release signal to the radiation irradiating apparatus 52 until the interlock release signals from all radiation image capturing apparatuses 1 are present. When the interlock release signals from all radiation image capturing apparatuses 1 are present, the interlock release signal can be transmitted to the radiation irradiating apparatus 52.

When the simple capturing and the long length capturing are performed using the non-linking method radiation image capturing apparatus 1, since the signal (irradiating start signal, interlock release signal, etc.) is not communicated between the radiation image capturing apparatus 1 and the radiation irradiating apparatus 52 as described above in the non-linking method, even if the radiation irradiating apparatus 52 transmits the irradiating start signal, the interlock release signal is not transmitted from the radiation image capturing apparatus 1 no matter how much time passes, and the radiation irradiating apparatus 52 is not able to irradiate radiation.

In this case, when the radiation irradiating apparatus 52 can be connected with the console C and the repeater 54, and the irradiating start signal can be transmitted from the radiation irradiating apparatus 52, a dummy signal corresponding to the interlock release signal can be transmitted from the console C and the repeater 54, and the radiation can be irradiated from the radiation irradiating apparatus 52. Then, when the radiation is irradiated from the radiation irradiating apparatus 52, the radiation image capturing apparatus 1 itself detects the start of irradiation of radiation and the state is advanced to the charge accumulating state. With this, accurate capturing is possible.

When the linking method radiation image capturing apparatus 1 and the non-linking method radiation image capturing apparatus 1 are loaded in a mixed state in the long length capturing bucky apparatus 51A when long length capturing is performed, for example, the console C is to grasp the linking method radiation image capturing apparatuses 1 loaded in the long length capturing bucky apparatus 51A, and repeats the communication of signals between the radiation irradiating apparatus 52 and the radiation image capturing apparatus 1. Then, the console C transmits the irradiating start signal transmitted from the radiation irradiating apparatus 52 to the linking method radiation image capturing apparatus 1. When the interlock release signals from the above radiation image capturing apparatuses 1 are present, the interlock release signals are transmitted to the radiation irradiating apparatus 52. With this, it is possible to accurately perform long length capturing in an example as described above.

[Example when Radiation Irradiating Apparatus does not Receive Interlock Control]

However, there are radiation irradiating apparatuses 52 which do not receive the above-described interlock control, and there are radiation irradiating apparatuses 52 which immediately irradiate radiation when the emitting switch 56 is fully pressed (see FIG. 5C). When the simple capturing or the long length capturing using the linking method radiation image capturing apparatus 1 is performed in the capturing room Ra provided with such radiation irradiating apparatus 52, the radiation is irradiated without the irradiating start signal being transmitted from the radiation irradiating apparatus 52.

Therefore, the radiation is irradiated while the radiation image capturing apparatus 1 is performing the reset processing of each radiation detecting element 7 before capturing, and the capturing cannot be accurately performed. When the radiation irradiating apparatus 52 is the apparatus which does not receive interlock control, the linking method radiation image capturing apparatus 1 cannot be used in the capturing.

When the radiation irradiating apparatus 52 provided in the capturing room Ra does not receive interlock control, and the linking method radiation image capturing apparatus 1 is selected as the radiation image capturing apparatus 1 to be used in the capturing, the console C or the alarm device in the capturing room Ra which receives the instruction from the console C can warn the user such as the radiology technician, etc. by sound or display that the selected radiation image capturing apparatus 1 cannot be used in the capturing.

[Configuration, Etc. of Bucky Apparatus]

According to the above description, for example, the console C is able to recognize the size of the radiation image capturing apparatus 1 or whether the radiation image capturing apparatus 1 loaded on the bucky apparatus 51 captures by the linking method or the non-linking method (for example, see FIG. 15, etc.).

Figure 19:
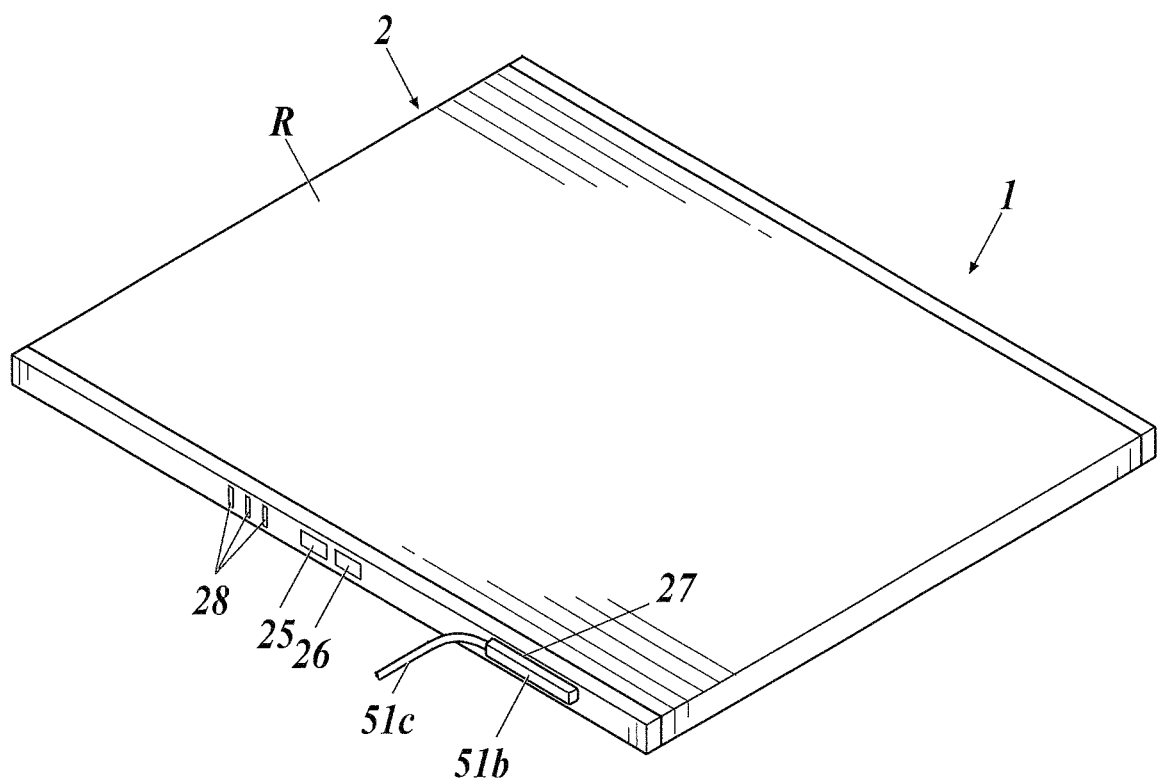
FIG. 19 is a diagram showing a state in which a connector of the bucky apparatus is connected to the connector of the radiation image capturing apparatus.

When the radiation image capturing apparatus 1 is loaded on the bucky apparatus 51, for example, as shown in FIG. 19, when the connector 27 (see FIG. 6) of the radiation image capturing apparatus 1 is connected with the connector 51b of the bucky apparatus 51, the cassette ID which is the identification information of the loaded radiation image capturing apparatus 1 and the identification information of the bucky apparatus 51 (hereinafter referred to as bucky ID) are transmitted to the console C from the bucky apparatus 51 through the cable 51c. Then, the console C holds in advance a list which associates the identification information of the radiation image capturing apparatus 1 in the facilities such as the hospital with the capturing method (linking method or non-linking method), size, etc. When the cassette ID and the bucky ID are transmitted from the bucky apparatus 51, the list is referred. With this, the console C is able to recognize which radiation image capturing apparatus 1 is loaded on which bucky apparatus 51.

The cassette ID, etc. of the radiation image capturing apparatus 1 can be read by a reading unit provided in the bucky apparatus 51, such as a tag reader or a barcode reader. The tag reader can read the above-described RFID tag. The barcode reader can read the barcode attached to the radiation image capturing apparatus 1 when the apparatus is loaded.

[Performing Long Length Capturing Using Bucky Apparatus not Including Connector]

In bucky apparatuses 51, there is a bucky apparatus 51 which is configured to be loaded with a cassette including conventional screen film or a CR cassette including a stimulable phosphor sheet. In such bucky apparatus 51, the above-described connector 51b is usually not provided.

Therefore, when the capturing is performed using such bucky apparatus 51, the radiation image capturing apparatus 1 cannot communicate the signal with the radiation irradiating apparatus 52 by wired communication through the connector 27 (see FIG. 6). Therefore, it is not always easy to perform capturing by the linking method. Consequently, it is preferable to load the non-linking method radiation image capturing apparatus 1 on the bucky apparatus 51 to perform capturing when the capturing is performed using the bucky apparatus 51 which is not provided with the connector 51b as described above.

According to the present embodiment, as described above, the console C judges whether to perform capturing by long length capturing or simple capturing based on the age P5 of the patient who is the subject, capturing site P7, etc. (see FIG. 11 and FIG. 12). When it is judged that the capturing to be performed is the long length capturing, the power consumption mode of the plurality of radiation image capturing apparatuses 1 in the capturing room Ra is switched from the power save mode to the capturing possible mode or the user such as the radiology technician, etc. operates the switching switch 26 (see FIG. 6) of the radiation image capturing apparatus 1 to allow the power consumption mode of the radiation image capturing apparatus 1 to be switched to the capturing possible mode.

However, in the long length capturing, the user such as the radiology technician, etc. needs to load, for example, three non-linking method radiation image capturing apparatuses 1 in the long length capturing bucky apparatus 51A which does not include the connector 51b. Therefore, there is a possibility that the user such as the radiology technician, etc. mistakes the non-linking method radiation image capturing apparatus 1 to be loaded. In this case, when the radiation image capturing apparatus 1 with the power consumption mode set in the power save mode is loaded by mistake, the radiation image capturing apparatus 1 cannot detect the start of irradiation of radiation and the image data D of the portion captured by this radiation image capturing apparatus 1 cannot be obtained. As a result, capturing needs to be performed again.

In order to prevent such situation, for example, when the long length capturing is performed by loading a plurality of non-linking method radiation image capturing apparatuses 1 in the long length capturing bucky apparatus 51A which does not include the connector 51b as described above, the console C can be configured to switch the power consumption mode of all of the non-linking method radiation image capturing apparatuses 1 in the capturing room Ra from the power save mode to the capturing possible mode. In such case, the console C can be configured so that the user such as the radiology technician, etc. operates the switching switch 26 of the non-linking method radiation image capturing apparatus 1 in the capturing room Ra to allow the power consumption mode to be switched to the capturing possible mode.

According to the above configuration, if the power consumption mode of all of the non-linking method radiation image capturing apparatuses 1 in the capturing room Ra are switched to the capturing possible mode, the non-linking method radiation image capturing apparatus 1 loaded on the long length capturing bucky apparatus 51A and irradiated with radiation detects the start of irradiation of radiation and advances to the charge accumulating state. Then, the image data D is accurately generated and the preview image data Dp and the image data D are transferred to the console C. The non-linking method radiation image capturing apparatus 1 which is not loaded in the long length capturing bucky apparatus 51A is not irradiated with radiation. Therefore, the non-linking method radiation image capturing apparatus 1 does not perform generating processing or transfer processing of the image data D.

Figure 18B:
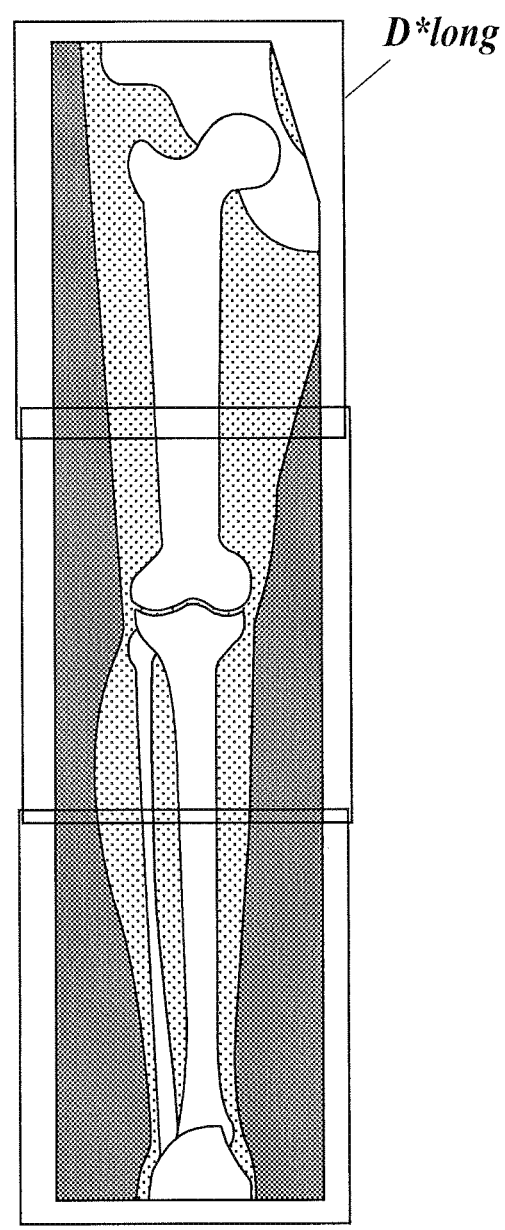
FIG. 18B is a diagram describing combining true image data calculated for each radiation image capturing apparatus in long length capturing to generate long length image data.

Consequently, according to the above configuration, even if the user makes a mistake and loads the wrong non-linking method radiation image capturing apparatus 1 to be loaded in the long length capturing bucky apparatus 51A, the image data D, etc. is transferred to the console C from only, for example, the three non-linking method radiation image capturing apparatuses 1 irradiated with radiation in the long length capturing. Therefore, the console C is able to accurately generate one long length image data D* by combining the plurality of pieces of image data D*1 to D*3 based on the image data D, etc. transferred from these radiation image capturing apparatuses 1 (see FIG. 18A and FIG. 18B). With this, the long length capturing can be accurately performed. Consequently, it is possible to accurately prevent the above-described situation in which capturing needs to be performed again.

In this case also, the following configuration can be provided. A tag reader which reads the RFID tag or a barcode reader which reads the barcode is attached to the long length capturing bucky apparatus 51A which does not include the connector 51b. The cassette ID, etc. of the loaded radiation image capturing apparatus 1 is read by a reading unit such as the tag reader or the barcode reader. When the loaded radiation image capturing apparatus 1 is different from the radiation image capturing apparatus 1 selected on the console C, a warning can be generated by sound or display.

[Long Length Capturing Using Bucky Apparatus Including Connector]

When the plurality of radiation image capturing apparatuses 1 are loaded on the long length capturing bucky apparatus 51A including the connector 51b to perform long length capturing, as shown in FIG. 19, the connector 51b of the bucky apparatus 51 is connected to the connector 27 of the radiation image capturing apparatus 1. With this, the radiation image capturing apparatus 1 is able to communicate signals with the radiation irradiating apparatus 52 through the cable 51c and the capturing can be performed by the linking method. Therefore, in this case, the linking method radiation image capturing apparatus 1 can be used as the radiation image capturing apparatus 1 loaded on the long length capturing bucky apparatus 51A including the connector 51b.

Even if the long length capturing bucky apparatus MA includes the connector 51b, similar to the above, the plurality of non-linking method radiation image capturing apparatuses 1 can be loaded on the bucky apparatus 51A to perform capturing. In this case, the plurality of non-linking method radiation image capturing apparatuses 1 are loaded in a state in which the connector 27 is connected to the connector 51b of the bucky apparatus 51A. Although signals are not communicated with the radiation irradiating apparatus 52 through the cable 51c (see FIG. 19), it is possible to receive supply of electric power from outside through the cable 51c.

Even if the long length capturing bucky apparatus 51A includes the connector 51b, when the radiation irradiating apparatus 52 is the apparatus which does not receive interlock control, the radiation image capturing apparatus 1 loaded on the long length capturing bucky apparatus 51A needs to be the non-linking radiation image capturing apparatus as described above.

[Judgement of Whether or not Long Length Capturing can be Performed by Console]

As described above, the connector 51b of the bucky apparatus 51A is connected to the connector 27 of the radiation image capturing apparatus 1 to transmit the cassette ID which is the identification information of the radiation image capturing apparatus 1 to the console C when the plurality of radiation image capturing apparatuses 1 are loaded on the long length capturing bucky apparatus 51A. Alternatively, the above-described tag reader or barcode reader reads the cassette ID of the loaded radiation image capturing apparatus 1 to transmit the cassette ID to the console C. With this, the console C is able to judge which radiation image capturing apparatus 1 is loaded in which loading position of the long length capturing bucky apparatus 51A. Therefore, the console C is able to judge whether it is possible to perform long length capturing in the above state.

In other words, the console C is able to judge whether the long length capturing can be performed based on the cassette ID of the loaded radiation image capturing apparatus 1 read with the reading unit such as the connector 51b of the long length capturing bucky apparatus 51A or the tag reader or the barcode reader.

Described below is an example in which the reading unit is the connector 51b of the bucky apparatus 51A. Alternatively, the reading unit such as the tag reader or the barcode reader can be provided in the loading position of the bucky apparatus 51A to perform the function similar to the connector 51b. In the example below, as shown in, for example, FIG. 20A, up to three radiation image capturing apparatuses 1 can be loaded on the long length capturing bucky apparatus 51A. Alternatively, the same description can apply when two radiation image capturing apparatuses 1 can be loaded or four or more radiation image capturing apparatuses 1 can be loaded.

Figure 20A:
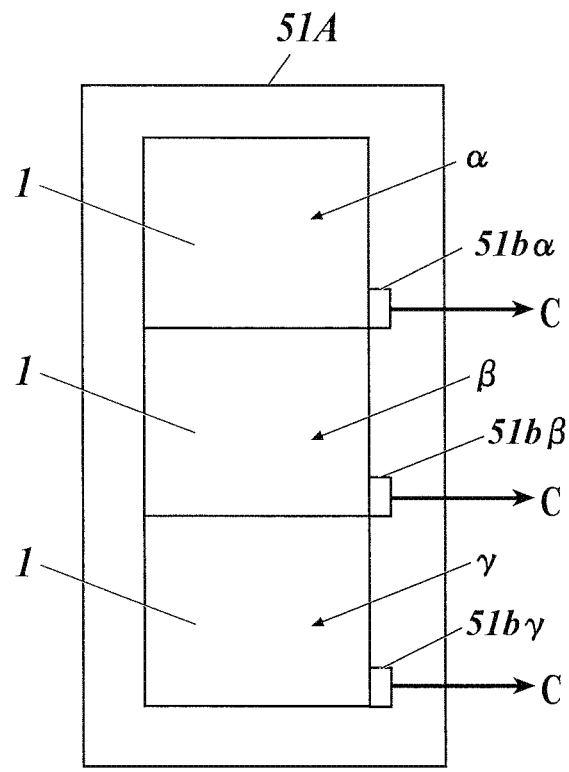
FIG. 20A is a diagram showing a state in which 3 radiation image capturing apparatuses are loaded on the bucky apparatus for long length capturing.

Specifically, as shown in the schematic diagram of FIG. 20A, for example, three loading positions α, β, and γ are provided in the long length capturing bucky apparatus 51A, and one radiation image capturing apparatus 1 can be loaded in each position, resulting in a total of three image capturing apparatuses 1. In this case, connectors 51bα, 51bβ, and 51bγ are provided in each respective loading position α, β, and γ of the bucky apparatus 51A. When the radiation image capturing apparatus 1 is loaded, the connectors 51bα, 51bβ, and 51bγ are each connected to the connector 27 (not shown in FIG. 20A, etc.).

When the connector 27 of the radiation image capturing apparatus 1 to be loaded is connected to any of the connectors 51bα, 51bβ, and 51bγ of the loading positions α, β, and γ, the long length capturing bucky apparatus 51A reads the cassette ID of the radiation image capturing apparatus 1 and transmits the read cassette ID with the identification information (hereinafter referred to as connector ID) of the connector 51b connected to the radiation image capturing apparatus 1 to the console C.

The console C associates the cassette ID and the connector ID transmitted from the long length capturing bucky apparatus 51A and stores and manages the above in the storage unit Cb. Moreover, the console C recognizes which radiation image capturing apparatus 1 is loaded in which loading position α, β, and γ of the long length capturing bucky apparatus 51A.

For example, as shown in FIG. 20A, when the radiation image capturing apparatus 1 is loaded in each loading position α, β, and γ of the long length capturing bucky apparatus 51A, the long length capturing can be performed. Then, when the console C judges that the long length capturing can be performed, the console C switches the power consumption mode of the plurality of radiation image capturing apparatuses 1 loaded on the long length capturing bucky apparatus 51A from the power save mode to the capturing possible mode to advance to the capturing possible state.

According to the above configuration, when the long length capturing can be performed, the plurality of radiation image capturing apparatuses 1 loaded on the long length capturing bucky apparatus 51A is advanced accurately to the capturing possible state. Therefore, the long length capturing can be accurately performed.

Although illustration is omitted, for example, the console C judges that the long length capturing cannot be performed when only one radiation image capturing apparatus 1 is loaded in any of the loading positions α, β, and γ of the long length capturing bucky apparatus 51A.

Figure 20B:
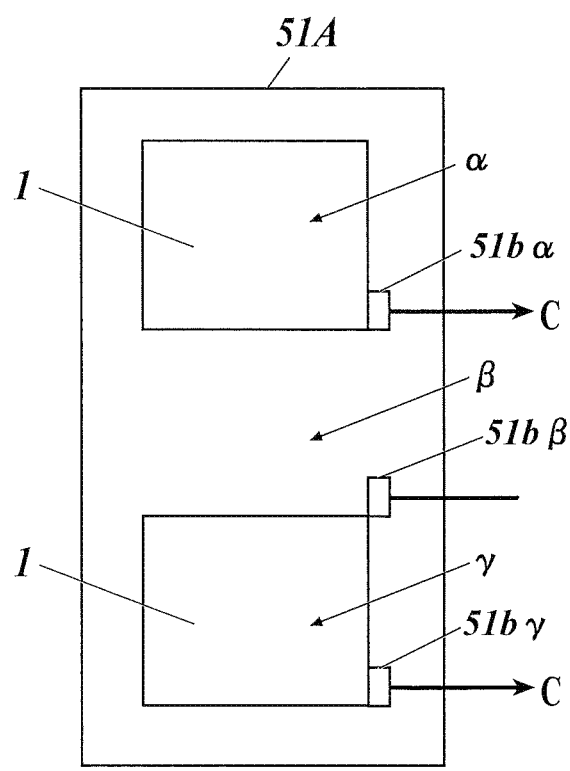
FIG. 20B is a diagram showing a state in which the radiation image capturing apparatus is not loaded on a center loading position of the bucky apparatus for long length capturing.

For example, as shown in FIG. 20B, even if a plurality of radiation image capturing apparatuses 1 are loaded on the long length capturing bucky apparatus 51A, if the loading positions where the plurality of radiation image capturing apparatuses 1 are loaded are not continuous, for example, the radiation image capturing apparatus 1 is loaded in the loading positions α and γ but the radiation image capturing apparatus 1 is not loaded in the loading position β in between, the long length capturing cannot be performed.

Therefore, the console C is configured to judge that the long length capturing cannot be performed when the loading positions α, β, and γ of the plurality of radiation image capturing apparatuses 1 loaded on the long length capturing bucky apparatus 51A are not continuous.

When the console C judges that the long length capturing cannot be performed even if the long length capturing bucky apparatus 51A is used (in other words, the radiation image capturing apparatus 1 is loaded), the console C notifies to the user such as the radiology technician, etc. that the long length capturing cannot be performed by, for example, display on the display unit Ca of the console C, generating sound, or through a notifying unit by sound or display provided in the capturing room Ra.

According to the above configuration, in a situation in which the long length capturing cannot be performed, it is possible to accurately notify that the long length capturing cannot be performed under the present conditions before the user such as the radiology technician, etc. allows the radiation to be irradiated from the radiation irradiating apparatus 52. With this, it is possible to accurately prevent the radiation being irradiated in a situation where long length capturing cannot be performed.

Although illustration is omitted, for example, if the radiation image capturing apparatus 1 in the loading position α is loaded in the loading position β or the radiation image capturing apparatus 1 in the loading position γ is loaded in the loading position β from the state as shown in FIG. 20B, the loading positions of the plurality of radiation image capturing apparatuses 1 are in a continuous state in the long length capturing bucky apparatus 51A. The following configuration is possible in which the console C judges that the long length capturing can be performed if the loading positions of the plurality of radiation image capturing apparatuses are continuous.

Although illustration is omitted, the following configuration is possible in which the user such as the radiology technician, etc. is warned by enlarging the display on the display unit Ca of the console C showing the state such as only one radiation image capturing apparatus 1 being loaded on the long length capturing bucky apparatus 51A or the loading positions α, β, and γ of the plurality of radiation image capturing apparatuses 1 not being continuous (see FIG. 20B) even when the long length capturing is performed.

The following configuration is possible in which the console C displays on the display unit Ca that the radiation image capturing apparatus 1 loaded in the loading position α is loaded in the loading position β, or the radiation image capturing apparatus 1 loaded in the loading position γ is loaded in the loading position β from the state shown in FIG. 20B, and the user judges whether the long length capturing can be performed with two radiation image capturing apparatuses 1.

For example, as shown in FIG. 20A, even if three radiation image capturing apparatuses 1 are loaded on the long length capturing bucky apparatus 51A, for example, as described above, when the radiation irradiating apparatus 52 is the apparatus which does not receive interlock control, the capturing cannot be performed if the linking method radiation image capturing apparatus 1 is loaded. Therefore, in such case, when it becomes clear that the loaded radiation image capturing apparatus 1 is the linking method radiation image capturing apparatus 1 based on the transmitted cassette ID, the console C judges that the long length capturing cannot be performed. Preferably, for example, the console C is configured to notify the user to load the non-linking method radiation image capturing apparatus 1 in such case.

[Size and Position of Plurality of Loaded Radiation Image Capturing Apparatuses]

Figure 21A:
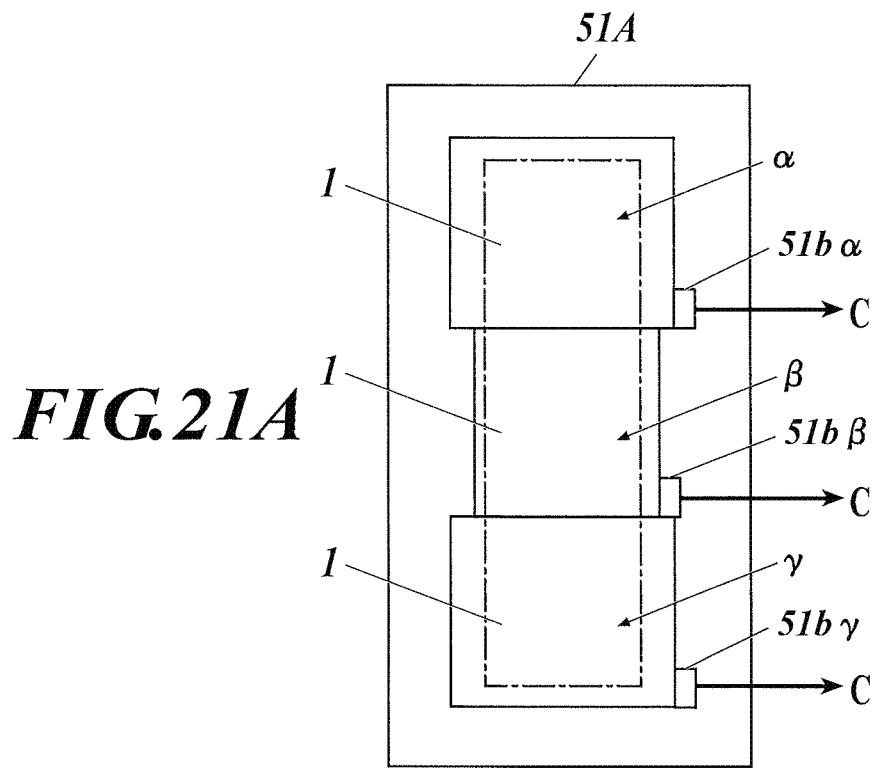
FIG. 21A is a diagram describing a state in which the 3 radiation image capturing apparatuses are loaded on the bucky apparatus for long length capturing in a center aligned position and an irradiating field in this state.

As shown in FIG. 21A, the plurality of radiation image capturing apparatuses 1 loaded on the long length capturing bucky apparatus 51A may each have a different size. FIG. 21A shows the radiation image capturing apparatus 1 with a size of 14×17 inches loaded in the loading positions α and γ, and the radiation image capturing apparatus 1 with a size of 14×14 inches loaded in the loading position β.

When the sizes of the plurality of radiation image capturing apparatuses 1 loaded in the long length capturing bucky apparatus 51 are different, for example, the radiation needs to be irradiated with the irradiating field narrowed as shown in the long and short dashed line of FIG. 21A so that the irradiated radiation does not fall out of the left and right boundaries of the radiation image capturing apparatus 1 with the smallest width (in the example shown in FIG. 21A, the radiation image capturing apparatus 1 in the loading position β with the size 14×14 inches).

For example, when it is judged that the sizes of the plurality of radiation image capturing apparatuses 1 loaded on the long length capturing bucky apparatus 51A are different based on the cassette ID of each radiation image capturing apparatus 1 transmitted from the long length capturing bucky apparatus 51A, the console C can be configured to notify a warning to the user such as the radiology technician, etc. to be cautious of the setting of the irradiating field of the radiation to be irradiated by displaying the warning on the display unit Ca or generating sound.

Figure 21B:
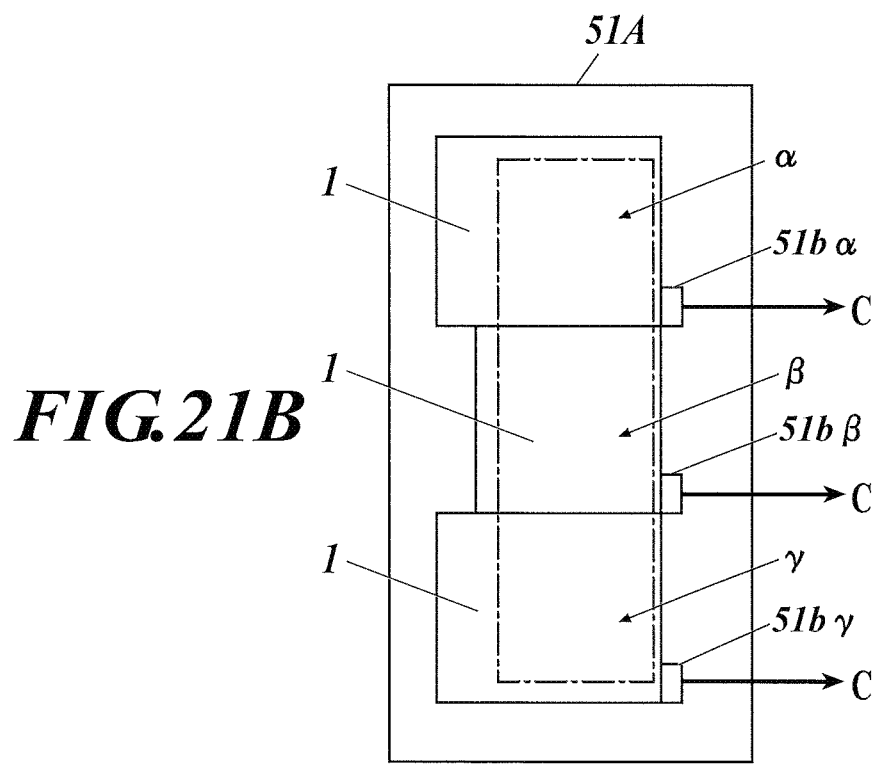
FIG. 21B is a diagram describing a state in which the 3 radiation image capturing apparatuses are loaded on the bucky apparatus for long length capturing in a right aligned position and an irradiating field in this state.
Figure 22:
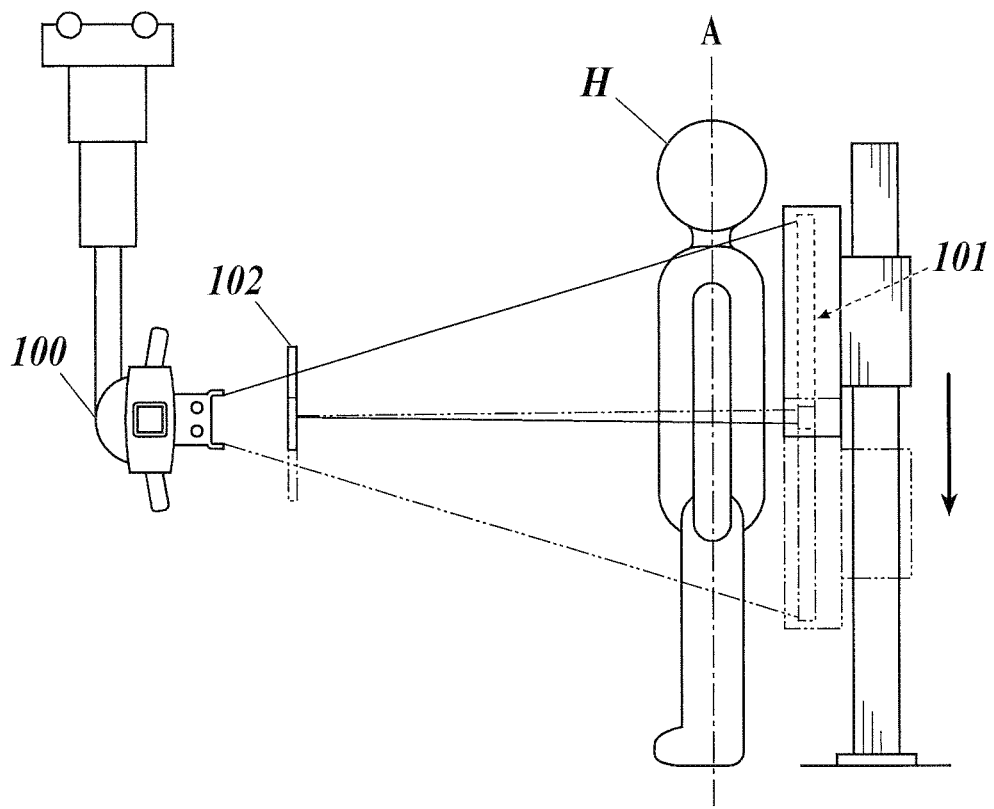
FIG. 22 is a diagram describing a conventional configuration of the radiation image capturing system which performs long length capturing.

When the sizes of the plurality of radiation image capturing apparatuses 1 loaded on the long length capturing bucky apparatus 51A are different as described above, as shown in FIG. 21A or FIG. 21B, for example, depending on whether the plurality of radiation image capturing apparatuses 1 are aligned at the center position (FIG. 21A) or the radiation image capturing apparatuses 1 are aligned to the right of the bucky apparatus 51A (FIG. 21B) or the radiation image capturing apparatuses 1 are aligned to the left (not shown), the position of the irradiating field of the radiation to be irradiated in the horizontal direction changes.

Therefore, although illustration is omitted, for example, a detecting unit can be provided to detect, in the horizontal direction, the position of the radiation image capturing apparatuses 1 loaded in the loading positions α, β, and γ in the long length capturing bucky apparatus 51A to display the positions of the radiation image capturing apparatuses 1 in the horizontal direction detected by the detecting unit on the display unit Ca of the console C. Alternatively, simply whether the image capturing apparatuses 1 are aligned at the center, to the right or to the left can be displayed. Alternatively, the display of the position of the radiation image capturing apparatuses 1 or the display of the aligning at the center, etc. can be displayed on a display unit provided in the long length capturing bucky apparatus 51A instead of or together with the display unit Ca of the console C.

According to the above configuration, the user such as the radiology technician, etc. is able to see the display and adjust the position of the irradiating field of the radiation irradiated to the long length capturing bucky apparatus MA according to the display. With this, the long length capturing can be accurately performed. Moreover, the console C is able to perform the above-described processing in the long length capturing such as the combining processing of the image data D*1 to D*3 or the generating processing of the long length image data D*long (see FIG. 18A, FIG. 18B) with recognition of the information such as the position of the radiation image capturing apparatuses 1 or the radiation image capturing apparatuses 1 being aligned to the center. From this point also, it is possible to accurately perform long length capturing.

[Synchronizing Non-Linking Method Radiation Image Capturing Apparatuses]

When radiation is irradiated with one shot from the radiation irradiating apparatus 52 to the radiation image capturing apparatuses 1 loaded on the long length capturing bucky apparatus 51A to perform long length capturing, there is a difference in the amount of radiation irradiated to each radiation image capturing apparatus 1. Since the irradiating field of the irradiated radiation is narrowed, the amount of delivered radiation becomes small in the radiation image capturing apparatus 1 loaded in the top and bottom loading positions α and γ compared to the radiation image capturing apparatus 1 loaded in the middle loading position β (see FIG. 20A). Therefore, it is assumed that the performance to judge the start of irradiation decreases.

In this case, when the non-linking method radiation image capturing apparatus 1 is loaded on the long length capturing bucky apparatus 51A, for example, a large amount of radiation reaches the radiation image capturing apparatus 1 loaded in the loading position β and therefore, the start of irradiation of radiation can be promptly detected. However, there is a possibility that the detection timing of the start of irradiation of radiation is delayed in the radiation image capturing apparatuses 1 loaded in the loading positions α and γ. When the detecting timing of the start of irradiation of radiation is different in each radiation image capturing apparatus 1, the timing that the image data D, etc. is transferred to the console C from each radiation image capturing apparatus 1 becomes different depending on each radiation image capturing apparatus 1, and the processing in the console C becomes difficult.

For example, in an example where the plurality of non-linking method radiation image capturing apparatuses 1 are loaded on the long length capturing bucky apparatus 51A, when the radiation image capturing apparatus 1 detects the start of irradiation of radiation, the detecting processing stops at this point, the state advances to the charge accumulating state (see FIG. 9), and the signal showing the above is transmitted to the console C. Then, when the console C receives the signal from the first radiation image capturing apparatus 1 which detected start of irradiation of radiation, the console C transmits an advancing signal to the other radiation image capturing apparatuses 1 loaded on the long length capturing bucky apparatus 51A. Then, when the other radiation image capturing apparatuses 1 receive the advancing signal from the console C, even if the other radiation image capturing apparatuses 1 themselves do not detect the start of irradiation of radiation, the detecting processing stops at this point and the state is advanced to the charge accumulating state.

According to such configuration, the plurality of non-linking method radiation image capturing apparatuses 1 loaded on the long length capturing bucky apparatus 51A advances to the charge accumulating state and the generating processing of the image data D and the processing thereafter can be performed at the same timing. With this, the display processing of the preview image p_pre and the generating processing of the long length image data D*long can be easily performed on the console C. According to such configuration, the time necessary for the entire long length capturing can be made shorter compared to when the radiation image capturing apparatuses 1 detect the start of irradiation of radiation at a different timing and the processing thereafter is performed. Consequently, the burden of the patient who is the subject can be reduced.

[Management of Position of Radiation Image Capturing Apparatus when Plurality of Capturing Rooms are Provided]

In order to achieve the objects of the present invention, which are to accurately perform both simple capturing and long length capturing using the radiation image capturing apparatus 1 and to perform efficient capturing, it is necessary to prevent mistaking the radiation image capturing apparatus 1 to be used in the capturing or the user such as the radiology technician, etc. having to search for the radiation image capturing apparatus 1.

Such situation occurs especially when the radiation image capturing system 50 includes a plurality of capturing rooms Ra (Ra1 to Ra3) associated with one or a plurality of consoles C (C1, C2) (see FIG. 2). In order to prevent the above situation, for example, as shown in FIG. 2, the radiation image capturing system 50 may be provided with a management apparatus S.

Specifically, as described above, when the radiation image capturing apparatus 1 is brought into the capturing room Ra and inserted in the cradle 55 (see FIG. 2 and FIG. 3), or the tag of the radiation image capturing apparatus 1 is read with the tag reader 60 (see FIG. 4) and the cassette ID which is the identification information of the radiation image capturing apparatus 1 is read, the cassette ID is transmitted and notified to the management apparatus S in addition to the console C through the repeater 54. Here, for example, the identification information of the repeater (hereinafter referred to as the repeater ID) is attached to the cassette ID and notified.

The management apparatus S is able to judge from which capturing room Ra the cassette ID is transmitted based on the repeater ID attached to the cassette ID, and becomes aware that the radiation image capturing apparatus 1 including the cassette ID is in the capturing room Ra corresponding to the repeater ID. The management apparatus S can also manage the information by storing the information in the storage unit Cb. Instead of or together with the repeater ID, the identification information of the cradle 55 or the identification information of the tag reader 60 can be attached to the read cassette ID and transmitted to the management apparatus S. As long as the capturing room Ra from which the cassette ID is transmitted can be reliably identified, the information attached to the cassette ID can be any type of information.

In reply to the request from the console C, the management apparatus S transmits information of the radiation image capturing apparatus 1 in the capturing rooms Ra to the console C. The console C is able to display the radiation image capturing apparatus 1 in each capturing room Ra in a form of a list on the display unit Ca as shown in, for example, Japanese Patent Application Laid-Open Publication No. 2012-105787, Japanese Patent Application Laid-Open Publication No. 2013-126604.

According to the above configuration, the user such as the radiology technician, etc. sees the list and is able to understand which radiation image capturing apparatus 1 belongs to which capturing room Ra. Here, as described above, for example, the following is displayed near the information of the radiation image capturing apparatuses 1. The linking method radiation image capturing apparatus 1 is displayed with blue and the non-linking method radiation image capturing apparatus 1 is displayed with red. The sizes such as 14×17 inches, 14×14 inches, and 17×17 inches are each displayed with design such as a square (solid colored), stripes, dots, etc. According to such configuration, the user such as the radiology technician, etc. is able to understand the capturing method and the size of the radiation image capturing apparatus 1 at a glance, and this is preferable.

In order to perform long length capturing more accurately, for example, the following configuration is possible. The long length capturing bucky apparatus 51A is provided in any or all of the capturing rooms Ra among the plurality of capturing rooms Ra.

As described above, the console C judges that the capturing to be performed is long length capturing based on the capturing order information, and the console C transmits to the management apparatus S a request signal requesting an answer regarding in which capturing room Ra the long length capturing can be performed. Then, in response to the above, the management apparatus S judges in which capturing room Ra the long length capturing can be performed based on the information of the radiation image capturing apparatus 1 in each capturing room Ra or information of which capturing room Ra includes the long length capturing bucky apparatus 51A. The management apparatus S notifies the capturing room Ra in which long length capturing can be performed to the console C. The console C can notify the information of the capturing room Ra notified from the management apparatus S to the user such as the radiology technician, etc. by displaying on the display unit Ca, for example.

As described above, depending on whether the radiation irradiating apparatus 52 receives interlock control or not, the type of radiation image capturing apparatus 1 (in other words, linking method or non-linking method) which can be used in the long length capturing may be limited. Moreover, depending on whether the connector 51b is provided in the long length capturing bucky apparatus 51A, the type of radiation image capturing apparatus 1 which can be used in the long length capturing may need to be considered.

If there are a plurality of radiation image capturing apparatuses 1 which can be used in the long length capturing using the long length capturing bucky apparatus 51A and the radiation irradiating apparatus 52 in the capturing room Ra provided with the long length capturing bucky apparatus 51A, the long length capturing can be performed in the capturing room Ra. However, if a plurality of such radiation image capturing apparatuses 1 are not present, the long length capturing cannot be immediately performed in the capturing room Ra.

Since the management apparatus S judges in which capturing room Ra the long length capturing can be performed based on the information of the radiation image capturing apparatus 1 in each capturing room Ra and the information such as the long length capturing bucky apparatus 51A, and the capturing room Ra which can perform long length capturing is notified to the user such as the radiology technician, etc. through the console C, the user is able to accurately perform the long length capturing in the notified capturing room Ra.

When the management apparatus S judges the long length capturing cannot be performed in any capturing room Ra, for example, the management apparatus S can notify to the console C the information showing in which capturing room Ra the radiation image capturing apparatus 1 which can be used in the long length capturing is present, and the console C can notify the information notified from the management apparatus S by, for example, displaying on the display unit Ca in a form of a list.

According to the above configuration, based on the above notification, the user such as the radiology technician, etc. is able to go to each capturing room Ra with the necessary radiation image capturing apparatus 1 to accurately and promptly collect the radiation image capturing apparatuses 1. Then, the user such as the radiology technician, etc. is able to bring the radiation image capturing apparatuses 1 into the capturing room Ra provided with the long length capturing bucky apparatus 51A, load the above into the long length capturing bucky apparatus 51A, and accurately perform the long length capturing.

[Modification]
[Modification 1]

As described above, the selection screen H3 (see FIG. 14 to FIG. 16) displaying the radiation image capturing apparatus 1 in the capturing room Ra with the icon I is displayed on the display unit Ca of the console C of the radiation image capturing system 50 of the present embodiment. However, the selection screen H3 can be configured so that the icon I corresponding to the radiation image capturing apparatus 1 which cannot be used in the capturing to be performed is not displayed on the selection screen H3 even if the radiation image capturing apparatus 1 exists in the capturing room Ra, so that the icon I corresponding to the radiation image capturing apparatus 1 which cannot be used in the capturing to be performed (in other words, capturing corresponding to the icon I (icon I2 in FIG. 13) displayed with focus on the screen H2 (see FIG. 13)) cannot be selected on the selection screen H3.

According to the above configuration, it is possible to accurately prevent the radiation image capturing apparatus 1 which cannot be used in the capturing from being selected on the selection screen H3 by mistake by the user such as the radiology technician, etc. Consequently, simple capturing and long length capturing can be accurately performed.

[Modification 2]

As described above, there are radiation image capturing apparatuses 1 which can perform capturing by both the linking method and the non-linking method. When such radiation image capturing apparatus 1 is used, if the radiation irradiating apparatus 52 does not receive interlock control and the non-linking method radiation image capturing apparatus 1 needs to be used in capturing, a signal can be transmitted from the console C to the radiation image capturing apparatus 1 to switch the capturing method of the radiation image capturing apparatus 1 to the non-linking method.

In other words, according to the type of radiation irradiating apparatus 52 provided in the capturing room Ra (in other words, for example, whether or not interlock control is received), or the type of the bucky apparatus 51 (in other words, whether or not the connector 51b is provided), the console C can switch the capturing method of the radiation image capturing apparatus 1 in the capturing room Ra to the capturing method suitable for the capturing room Ra between the linking method and the non-linking method.

According to such configuration, the capturing method of the radiation image capturing apparatus 1 can be suitably switched between the linking method and the non-linking method depending on the state of the capturing room Ra, in other words, the type of the radiation irradiating apparatus 52 and the type of the bucky apparatus 51 and the capturing can be performed. Consequently, the simple capturing and the long length capturing can be accurately performed.

[Modification 3]

The above-described embodiment and modification show an example performing long length capturing by loading a plurality of radiation image capturing apparatuses 1 in the cassette holder 51a (see FIG. 1, etc.) when the long length capturing bucky apparatus 51A is used. Other than the above, for example, the radiation image capturing apparatus 1 loaded on the long length capturing bucky apparatus 51A can be used to perform simple capturing.

Specifically, although illustration is omitted, for example, a moving apparatus to move the loaded radiation image capturing apparatus 1 can be provided in the cassette holder 51a of the long length capturing bucky apparatus 51A, and the radiation image capturing apparatus 1 loaded in the cassette holder 51a of the long length capturing bucky apparatus 51A can be moved in an arbitrary position in the body axis A direction (see FIG. 1) of the subject H in the cassette holder 51a.

In this case, when the long length capturing bucky apparatus 51A is for standing position capturing, the moving apparatus is configured so that the loaded radiation image capturing apparatus 1 is able to move in the vertical direction in the cassette holder 51a. When the long length capturing bucky apparatus 51A is for lying position capturing, the moving apparatus is configured so that the loaded radiation image capturing apparatus 1 is able to move in the horizontal direction in the cassette holder 51a.

According to such configuration, the radiation image capturing apparatus 1 can be positioned in the capturing site of the subject H by moving the radiation image capturing apparatus 1 in the cassette holder 51a of the long length capturing bucky apparatus 51A. Therefore, since the posture of the subject H does not have to be moved and the position of the cassette holder 51a does not have to be changed depending on the capturing site of the subject H, the ease of use for the user such as the radiology technician, etc. is enhanced.

When the radiation image capturing apparatus 1 is moved in the cassette holder 51a as described above in a state in which the plurality of radiation image capturing apparatuses 1 are loaded on the cassette holder 51A of the long length capturing bucky apparatus 51A, and the simple capturing is performed, preferably, for example, the radiation image capturing apparatus 1 which is not used in the capturing is able to evacuate in the cassette holder 51a to a direction away from the subject H. According to such configuration, the radiation image capturing apparatus 1 to be used in capturing can be accurately moved in the cassette holder 51a of the long length capturing bucky apparatus MA and capturing can be performed without being interfered by the radiation image capturing apparatus 1 which is not used in the capturing.

According to the above-described embodiments, as shown in FIG. 1, etc., as the radiation irradiating apparatus 52, the wide angle irradiating type radiation irradiating apparatus is used. Such radiation irradiating apparatus is able to irradiate radiation to the plurality of radiation image capturing apparatuses 1 loaded on the long length capturing bucky apparatus 51A simultaneously (in other words, with one shot). Therefore, when the radiation image capturing apparatus 1 is moved in the cassette holder 51a of the long length capturing bucky apparatus 51A to perform simple capturing, the position and the irradiating direction of the radiation irradiating apparatus 52 do not necessarily have to be changed. (In this case also, the irradiating field of the radiation is narrowed to the necessary range so that the amount of irradiation to the subject H does not increase.)

However, preferably, in simple capturing, the radiation irradiating apparatus 52 is moved synchronizing with the movement of the radiation image capturing apparatus 1 in the cassette holder 51a and then the radiation is irradiated.

In other words, for example, when the long length capturing bucky apparatus 51A is for standing position capturing, and if the radiation image capturing apparatus 1 is moved to the position at the top edge in the cassette holder 51a, if the radiation irradiating apparatus 52 is the wide angle irradiating type, the radiation can be irradiated to the radiation image capturing apparatus 1 in the top edge position in the cassette holder 51a without changing the position (height) and the irradiating direction of the radiation irradiating apparatus 52. However, in this case, capturing is performed by irradiating the radiation to the radiation image capturing apparatus 1 from the bottom side, and the physician who interprets the generated radiation image p may feel that something is wrong with the image.

Therefore, when the simple capturing is performed by moving the radiation image capturing apparatus 1 in the cassette holder 51a of the long length capturing bucky apparatus 51A as described above, preferably, the radiation irradiating apparatus 52 is moved synchronizing with the movement of the radiation image capturing apparatus 1 in the cassette holder 51a so that the position (height) of the radiation irradiating apparatus 52 becomes the same position (height) as the radiation image capturing apparatus 1, and the capturing is performed.

The present invention is not limited to the above-described embodiments, and the present invention can be suitably modified without leaving the scope of the present invention.

What is claimed is:

1. A non-transitory computer readable storage medium storing a program performed in a computer used in a radiation image capturing system which is able to perform long length capturing by irradiating radiation on three radiation image capturing apparatuses provided on a radiographing table, the program comprising a step of:
   prohibiting long length capturing when a plurality of radiation image capturing apparatuses are not continuously provided on the radiographing table in a direction orthogonal to the radiation irradiation direction, by determining if each of the plurality of radiation image capturing apparatuses are connected to a connector of the radiographing table.

2. The storage medium according to claim 1, wherein in the prohibiting, when two radiation image capturing apparatuses are provided on the radiographing table, when the two radiation image capturing apparatuses are not continuously provided on the radiographing table in a direction orthogonal to the radiation irradiation direction, the long length capturing is prohibited.

3. The storage medium according to claim 1, wherein in the prohibiting, when only one radiation image capturing apparatus is provided on the radiographing table, the long length capturing is prohibited.

4. A controlling apparatus used in a radiation image capturing system which is able to perform long length capturing by irradiating radiation on three radiation image capturing apparatuses, comprising:
   a controller,
   wherein when a plurality of radiation image capturing apparatuses are not determined to be continuously provided on a radiographing table in a direction orthogonal to the radiation irradiation direction, long length capturing is prohibited, by determining if each of the plurality of radiation image capturing apparatuses are connected to a connector of the radiographing table.

5. The controlling apparatus according to claim 4, wherein, when two radiation image capturing apparatuses are provided on the radiographing table, when the two radiation image capturing apparatus are not continuously provided on the radiographing table in a direction orthogonal to the radiation irradiation direction, the long length capturing is prohibited.

6. The controlling apparatus according to claim 4, wherein, when only one radiation image capturing apparatus is provided on the radiographing table, the long length capturing is prohibited.

7. A system which is able to perform long length capturing by irradiation on three radiation image capturing apparatuses, comprising:
- three radiation image capturing apparatuses; and
- controlling apparatus which prohibits long length capturing when a plurality of radiation image capturing apparatuses are not continuously provided on a radiographing table in a direction orthogonal to the radiation irradiation direction, by determining if each of the plurality of radiation image capturing apparatuses are connected to a connector of the radiographing table.

8. The system according to claim 7, wherein, when two radiation image capturing apparatuses are provided on the radiographing table, when the two radiation image capturing apparatuses are not continuously provided on the radiographing table in a direction orthogonal to the radiation irradiation direction, the controlling apparatus prohibits the long length capturing.

9. The system according to claim 7, wherein, when only one radiation image capturing apparatus is provided on the radiographing table, the controlling apparatus prohibits the long length capturing.

* * * * *